(12) United States Patent
Giap

(10) Patent No.: US 10,561,522 B2
(45) Date of Patent: Feb. 18, 2020

(54) PATIENT POSITIONING DEVICE

(71) Applicant: BCG Medical, LLC, San Diego, CA (US)

(72) Inventor: Brandon Cuongquoc Giap, San Diego, CA (US)

(73) Assignee: BCG Medical, LLC, San Diego, CA (US)

( * ) Notice: Subject to any disclaimer, the term of this patent is extended or adjusted under 35 U.S.C. 154(b) by 449 days.

(21) Appl. No.: 15/386,643

(22) Filed: Dec. 21, 2016

(65) Prior Publication Data

US 2017/0112655 A1    Apr. 27, 2017

Related U.S. Application Data

(63) Continuation-in-part of application No. 13/764,809, filed on Feb. 12, 2013, now abandoned, which is a (Continued)

(51) Int. Cl.
*A61F 5/37* (2006.01)
*A61M 5/52* (2006.01)
(Continued)

(52) U.S. Cl.
CPC ............ *A61F 5/3761* (2013.01); *A61B 46/20* (2016.02); *A61G 7/1023* (2013.01);
(Continued)

(58) Field of Classification Search
CPC ........ A61F 5/3761; A61F 5/37; A61F 5/3715; A61F 5/3723; A61F 5/3746;
(Continued)

(56) References Cited

U.S. PATENT DOCUMENTS

| 4,939,801 A | 7/1990 | Schaal et al. |
| 5,775,967 A * | 7/1998 | Lacoursiere ............ B63C 9/115 |
| | | 441/115 |

(Continued)

OTHER PUBLICATIONS

International Search Report and Written Opinion in PCT/US2017/028785, dated Jul. 17, 2017.

*Primary Examiner* — Anna K Kinsaul
*Assistant Examiner* — Camtu T Nguyen
(74) *Attorney, Agent, or Firm* — Berger Singerman LLP; Geoffrey Lottenberg

(57) ABSTRACT

A patient positioning device includes a planar sheet having removably connected padded substrates attached proximal to the patient's arms. The padded substrates are wrapped around the patient's respective arms to protect and elevate the arms from the underlying table or gurney. Leggings are also provided to protect the patient's legs. The padded substrates include splits to allow wires and cables to pass through without getting tangled. A secondary sheet is attachable to the device to cocoon the patient when the patient is rolled over. A shoulder strap is provided under the patients shoulders, wrapping around and over the shoulders at the trapezius and at the shoulder cuff and is secured to the padded substrates for additional protection and security. The device has a low friction bottom surface to ease transfer and positioning.

2 Claims, 33 Drawing Sheets

Related U.S. Application Data continuation-in-part of application No. 13/153,432, filed on Jun. 5, 2011, now Pat. No. 8,661,580.

(60) Provisional application No. 62/326,116, filed on Apr. 22, 2016, provisional application No. 61/351,469, filed on Jun. 4, 2010.

(51) Int. Cl.
    *A61M 16/00*     (2006.01)
    *A61B 46/20*     (2016.01)
    *A61G 7/10*     (2006.01)

(52) U.S. Cl.
    CPC ......... *A61G 7/1026* (2013.01); *A61G 7/1063* (2013.01); *A61G 7/1092* (2013.01); *A61M 5/52* (2013.01); *A61M 16/0003* (2014.02); *A61G 7/109* (2013.01); *A61G 2210/90* (2013.01)

(58) Field of Classification Search
    CPC ... A61F 5/3769; A61F 5/3776; A61G 7/1023; A61G 7/1026; A61G 7/1063; A61G 7/1084; A61G 7/1092; A61M 5/52; A63B 46/00; A63B 46/20; A63B 46/27; A63B 46/40; A63B 2046/201; A63B 2046/205
See application file for complete search history.

(56) References Cited

U.S. PATENT DOCUMENTS

| | | | |
|---|---|---|---|
| 6,789,265 B1 * | 9/2004 | Vonrinteln | A41B 13/103 2/48 |
| 2006/0046589 A1 * | 3/2006 | Farley | B63B 35/79 441/108 |
| 2013/0152950 A1 | 6/2013 | Giap | |
| 2013/0198950 A1 | 8/2013 | Purdy et al. | |
| 2014/0366271 A1 | 12/2014 | Marshall et al. | |

* cited by examiner

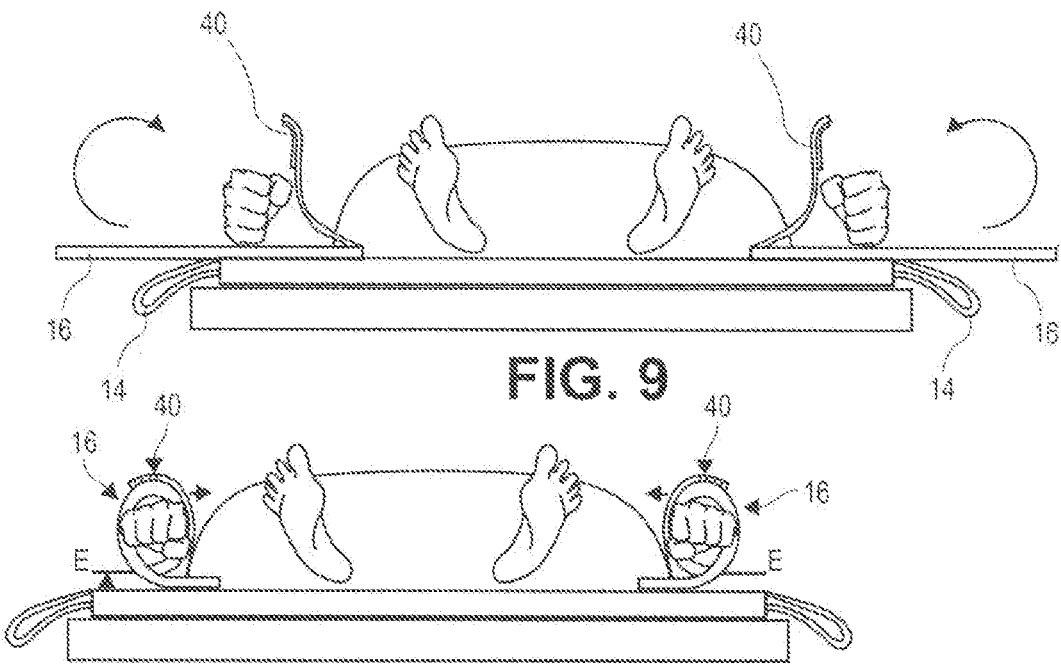
FIG. 9
FIG. 10
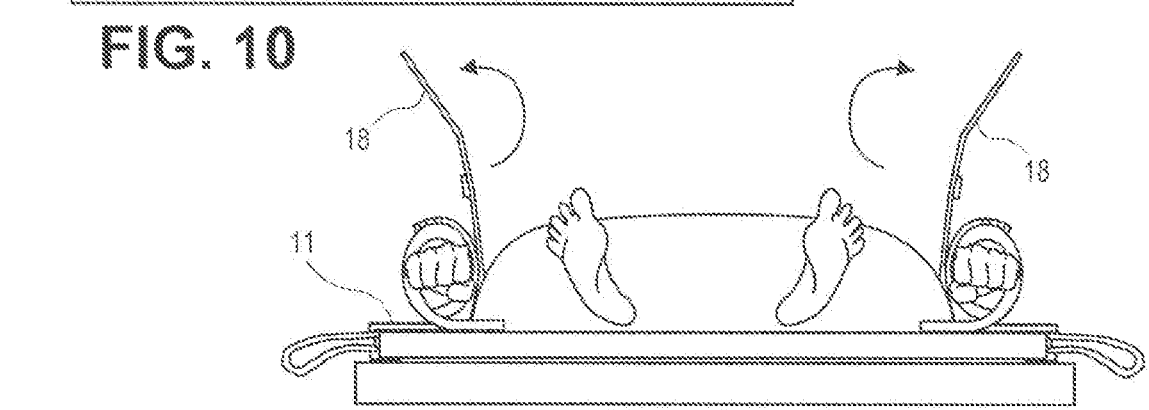
FIG. 11
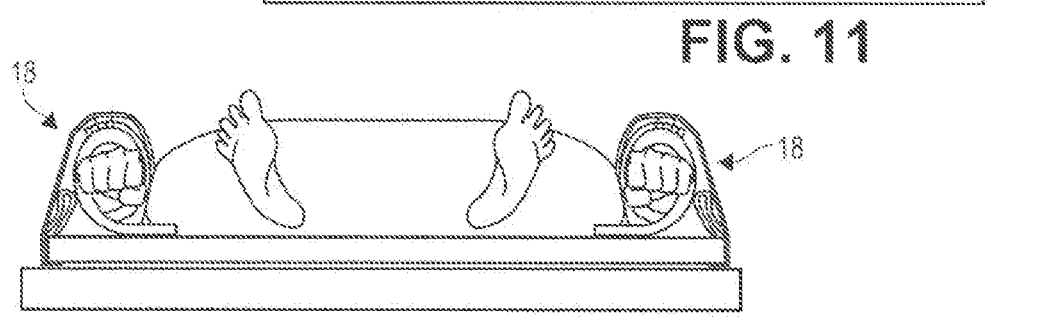
FIG. 12

PATIENT POSITIONING DEVICE

CROSS REFERENCE TO RELATED APPLICATIONS

This application is a continuation-in-part of U.S. patent application Ser. No. 13/764,809 filed on Feb. 12, 2013, which is a continuation-in-part of U.S. patent application Ser. No. 13/153,432 filed on Jun. 5, 2011, now U.S. Pat. No. 8,661,580, which claims priority to U.S. Provisional Application No. 61/351,769 filed on Jun. 4, 2010. This application also claims priority to U.S. Provisional Application No. 62/326,116 filed on Apr. 22, 2016.

BRIEF DESCRIPTION OF THE DRAWINGS

FIG. 9 depicts an end view of one embodiment of the as-used position of the device, prior to engagement of the padded substrates.

FIG. 10 depicts one embodiment of the device in an as-used mode, with the padded substrates engaged, securing the patient's arms, while elevating the arms a distance "E" above the support surface.

FIG. 11 depicts the engagement of the overlap substrates which are wrapped over the patient's arms.

FIG. 12 depicts the device with the overlap substrates wrapped over the patient's arms and are tucked under the mattress pad.

DETAILED DESCRIPTION

Figure 1:
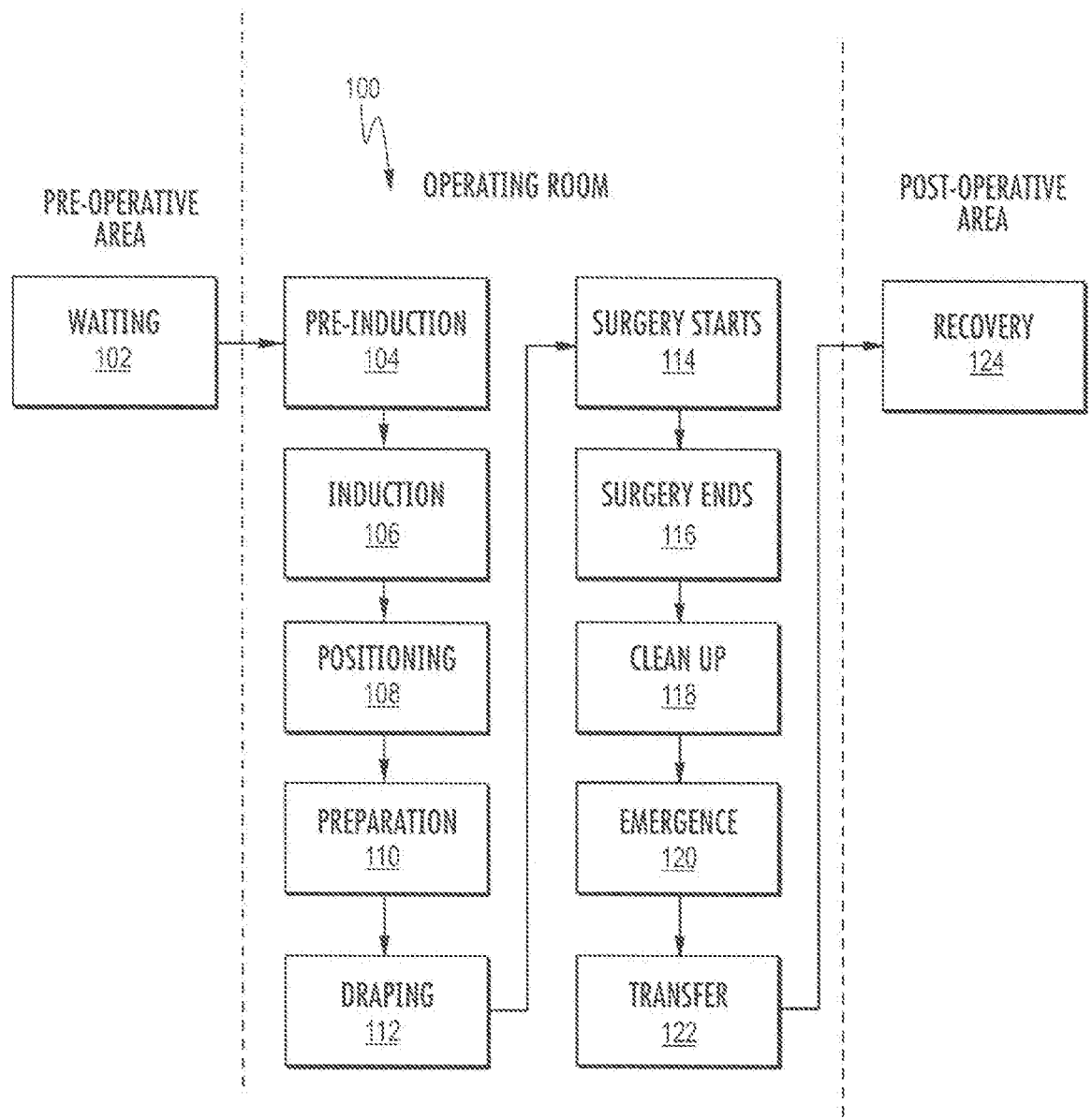
FIG. 1 is a flowchart of an embodiment of surgical events to which the present invention is relevant.

A patient experiences a multitude of stages when undergoing surgery. FIG. 1 is a flowchart of possible surgical events 100. The process starts in a pre-operative area. At step 102, the patient waits here before entering the operating room for surgery. Next, the patient is transferred into the operating room and at step 104, the pre-induction phase begins. The patient is placed on any necessary monitors such as blood pressure cuffs, Electrocardiography (EKG) electrodes, pulse oximeter, intravenous therapy (IV), or the like. At step 106, or induction, the patient is administered anesthesia for surgery.

At step 108, the patient is positioned for surgery. Depending on the type of surgery, the patient may be positioned in a prone, supine, lithotomy or lateral decubitus position. During this time the patient's body parts are often exposed to cold, ambient air normal in an operating room. Loss of body heat is a concern during the surgical process and the patient's body may become hypothermic.

Hypothermia may occur during the surgical process. Under anesthesia there may be a loss of the behavioral response to cold and impairment of thermoregulatory heat-preserving mechanisms through the hypothalamus and autonomic nervous system. Anesthetics also cause peripheral vasodilation, causing redistribution of the blood volume with associated heat loss, leading to significant reduction of core temperature. In addition to this, patients may be exposed during their surgery, further accelerating heat loss, and may already have become cold during the inactive period waiting for surgery. With fluid deprivation, conventionally practiced for up to 6-8 hours before general anesthesia, the patient may also become relatively dry and poorly perfused so that heat distribution by their circulation is further impaired. Finally, although steps may be taken to avoid it, un-warmed anesthetic gases and intravenous infusions may also add to the reduction of core temperature.

At step 110, the patient is prepared for surgery: This involves preparing the patient's skin area for surgical incision by using an antiseptic solution to help reduce infection. Further heat loss from the patient's body may occur. Next, draping the patient occurs at step 112. During this stage, the patient's incision area is isolated and exposed for surgery, while the remainder of the body is typically covered with sterile drapes. These sterile drapes are normally made of thin polypropylene material providing minimal heat loss prevention while the primary purpose is to provide a sterile environment to reduce infection during the surgery.

At step 114, surgery starts. Depending on the procedure, surgery may be short or last several hours. Again, additional heat loss from the patient's body may occur. At step 116, surgery ends.

Clean up starts at step 118. The patient, sheets, coverings and instruments are cleaned and removed from soiling due to body fluids. At step 120, the patient begins to emerge from anesthesia and may be awaken by medical personnel. The patient is then moved to a transporting gurney at step 122 and transferred to a recovery room entering the post-operative area. At step 124, the patient further recovers from anesthesia.

As is evident, a patient undergoing an operation or other procedure will be moved, positioned, re-positioned and transported several time. Accordingly, the present invention provides a patient positioning device that can be used for moving and lifting a patient from one surface to another surface in a hospital setting. Examples of such a device are described that are adapted for easy lifting of a patient, to and from an operating table, which offers ease of use for lifting the patient and protection of the patient's arms and legs during surgery and transport.

Figure 2:
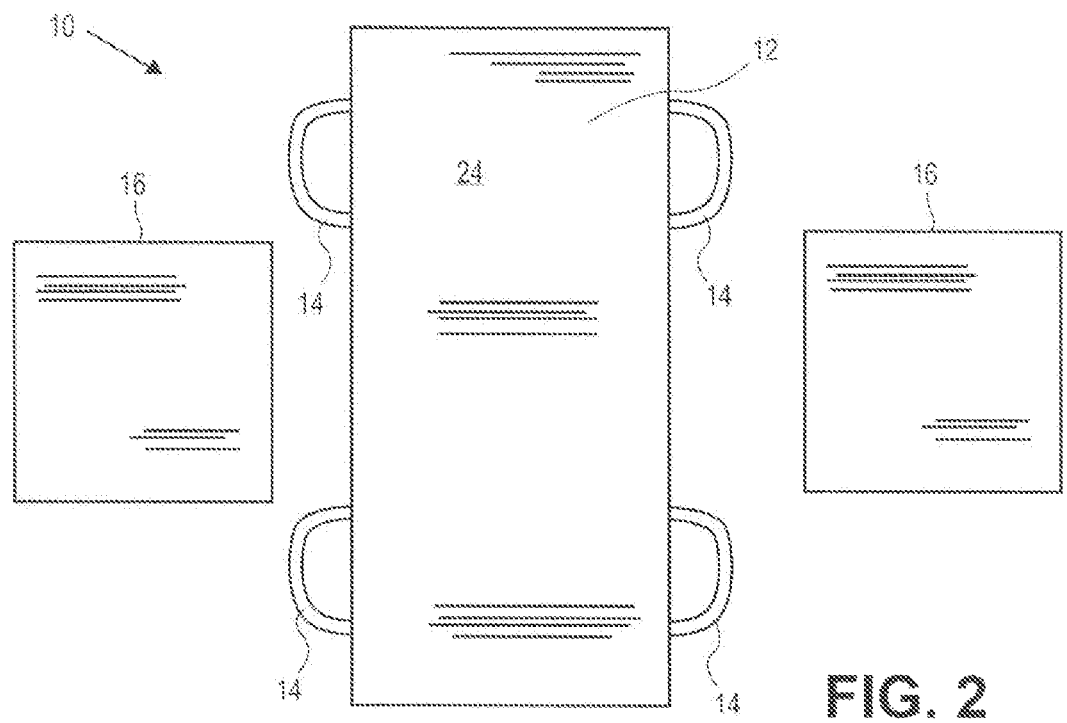
FIG. 2 depicts one embodiment of the patient positioning device.
Figure 3:
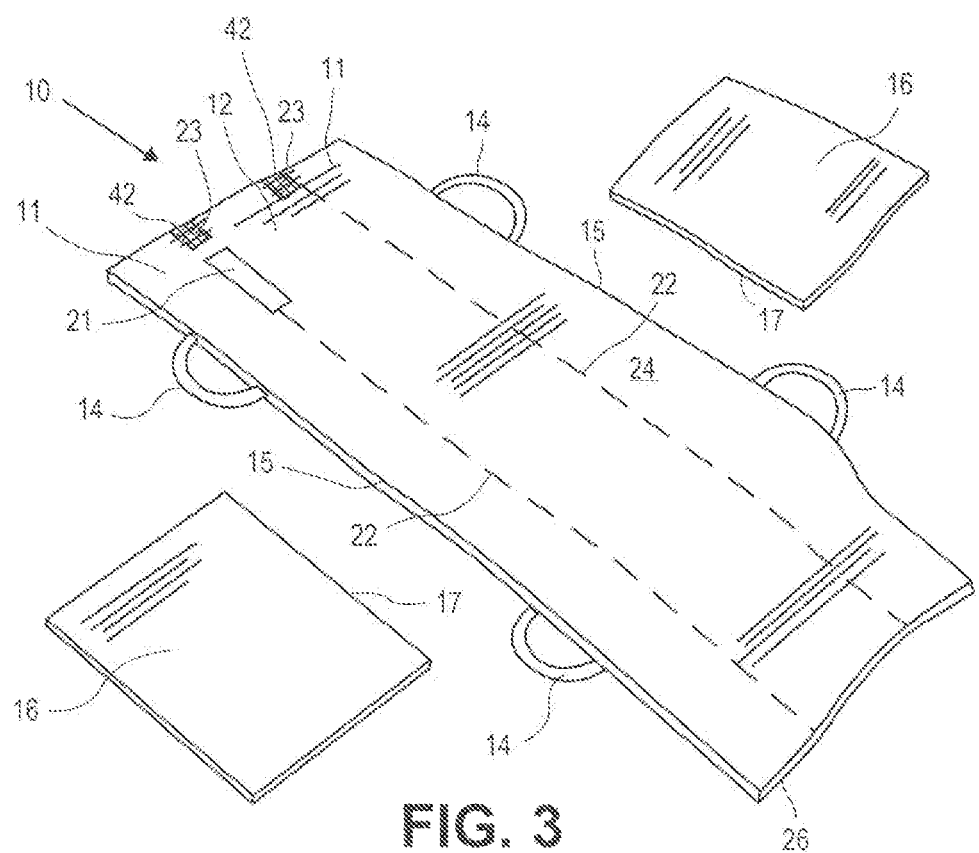
FIG. 3 depicts a perspective view of one embodiment of the device.

FIGS. 2 and 3 show one embodiment of the patient positioning device 10 of the present invention. A top surface 24 is positioned opposite the bottom surface 26. The top surface 24 and bottom surface 26 are formed of flexible fabric sheet and composed of center section 12, overhang sections 11, outer edge of center section 22 and outer edge of overhang sections 15. The center section 12 is of a rectangular geometry and adapted in length and width to accommodate the size and shape of a human being. Further, the center section 12 is sized to be laid on an operating room table which varies between, for example, 20-24 inches, or a stretcher or gurney with a width between, for example, 22-27 inches. Overhang sections 11 extend from the sides of center section 12. These overhang sections may be tucked under the mattress or pad on a gurney or table providing a means for the device 10 to operate in place of a bed sheet thus reducing germs and cost. Outer edge of center section 22 is a point of attachment for various components described hereafter.

Handles 14 are attached to outer edge of overhang sections 15 which allow for a safe grip on the device when used for lifting and pulling the device after the patient is secured. The quantity and orientation of handles 14 is not limited by the drawing as shown but is merely simplified for illustrative purposes.

The top and bottom surface, 24 and 26 respectively, may be of different material each of which is adapted for a specific purpose. The top surface 24 may be made of textile or paper reinforced with textile fabric, or another woven or knitted fabric adapted to the task of supporting a patient thereon. The bottom surface 26 of the device may have a surface configured to have low friction when the device 10, with patient aboard, is slid during a transition. The bottom surface 26 is composed of material which is slippery or has a low coefficient of friction, so as to allow the medical staff a means to easily slide the patient to and from a support surface. One example for a top surface 24 is a paper cloth or similar woven or knitted textile surface. The bottom surface which is exposed, may be formed of any low friction material as would occur to those skilled in the art including but not limited to one or a combination of materials from a group including PTFE impregnated or coated fabric, spunbond or other fabric when woven or formed has a slippery surface, or fabrics such as rip-stop or micro fiber-based materials woven or knitted from woven nylon, or polyester. The slippery bottom surface 26 may be sewn or laminated or coated to the device 10 or on the opposite side of the material forming the top surface 24 of the center section 12.

Referring to FIG. 3, equipment straps 23 and pocket 21 are detailed. Equipment straps 23 are fastened to top surface 24 at one end and contain hook and loop fasteners. Directly under equipment straps 23, and coupled to top surface 24, is a group 42 of hook and loop fasteners. The equipment straps 23 are fastened to group 42. Pocket 21 is coupled to top surface 24 having one open end. Both equipment straps 23 and pocket 21 may be used to secure a medical device, an intravenous tube, a catheter tube and/or a piece of medical equipment that is attached directly to the patient.

FIGS. 2 and 3 also show two disengaged padded substrates 16 which are substantially planar. These padded substrates 16 are flexible and have an inner edge 17 that may be permanently fastened to center section 12 by sewing with durable thread or another suitable means, or temporarily fastened with a hook and loop fastener, such as Velcro® or other such removable fasteners. In one embodiment, padded substrates 16 are temporarily removed from device 10 so they may be employed on pre-existing patient transfer devices as described in the prior art which lack protection for the patient's arms.

Padded substrates 16 are positioned with respect to the top edge of the central area of the center section 12 at a distance comparable to the distance of a human arm, between the upper arm and hand, when placed to the side, to the human head. Preferably, padded substrates 16 have a layer of padding imbedded or engaged such that when engaged around the arm of a patient, a means to pad the arm is provided. This protects the patient's arm from any pressure forces imparted by the table or by a surgeon. Padded substrates 16 also are configured to engage around the arms of the patient, and hold them against their body and slightly elevated from the underlying table or support surface. This helps eliminate injury to the patient's arm when it is supported on a hard table surface for a long duration by placing a gap between the table and arm.

Figure 4:
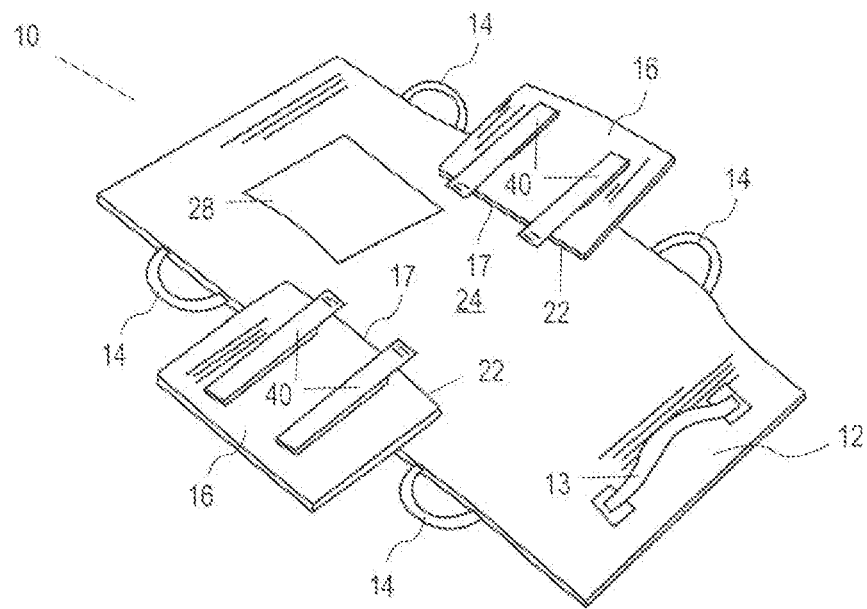
FIG. 4 depicts an assembled view of one embodiment of the device also showing straps and foot securement restraints and an optional non-slip pad.

Referring to FIG. 4, padded substrates 16 are shown attached at inner edge 17 to the center section 12. The back surface of padded substrates 16 have strips of hook and loop fasteners for securing. Straps 40 are also attached to the center section 12 at outer edge of center section 22 at one end. The bottom side of straps 40 have hook and loop fasteners for securing to padded substrates 16 when padded substrates 16 are wrapped around a patient's arm.

Optionally, device 10 may employ a permanent or removably engageable non-slip pad 28. The non-slip pad 28 will provide a means to prevent sliding when the patient is positioned on an angle. Also, in a one embodiment, foot securement restraint 13 is provided. The foot securement restraint 13 is coupled to top surface 24 and is wrapped around the legs of the patient and may be held by hook and loop fasteners. This foot securement restraint 13 enables the lower leg to remain positioned and secured during lifting or sliding of device 10.

Figure 5:
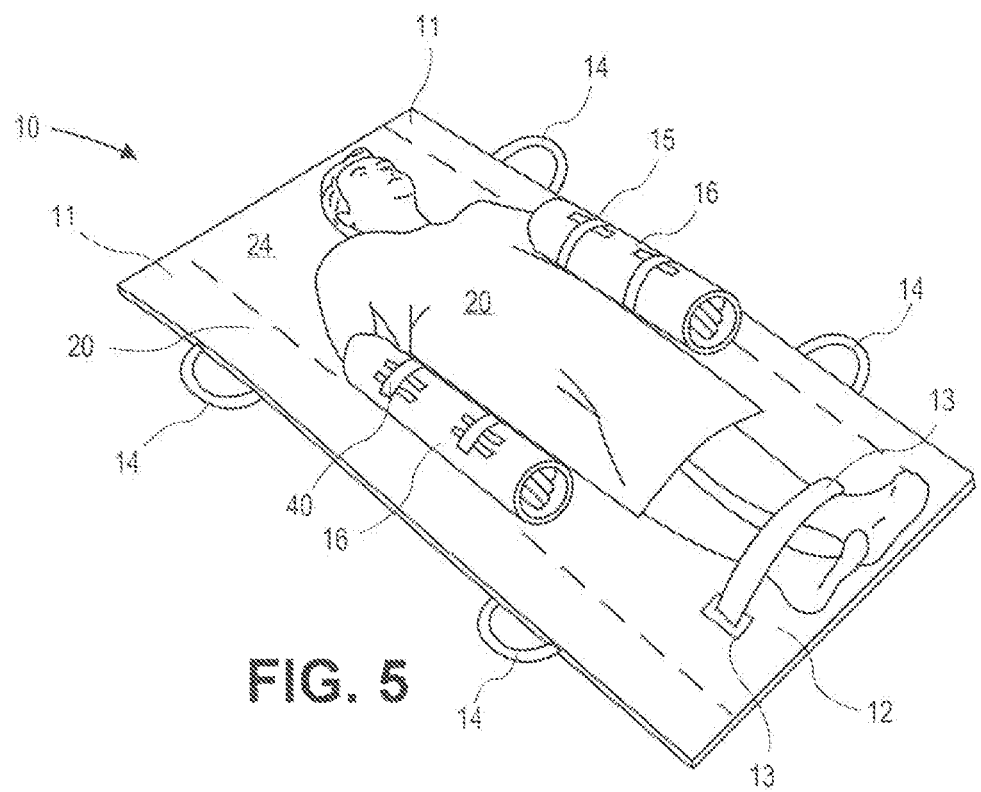
FIG. 5 depicts an example of one embodiment of the device in the as-used position with the patient's arms wrapped in the padded flexible substrates and lower legs secured.

In use, padded substrates 16 are employed to encircle and support a patient's arm when a patient lays on the center section 12 surface. This arm wrapping by the padded substrates 16 provide protection against the patient's arm moving outside the table area during fatigue and a potential pressure injury from contact with the underlying table or with a leaning surgeon while on an operating table. FIG. 5 illustrates the device 10 with the patient 20 positioned with both arms encircled within padded substrates 16. Patient 20 is positioned on the patient positioning device 10 and straps 40 are employable to hold the flexible, padded substrates 16 in wrapped configuration around the patient's arms and maintain the arms close to their body and out of the way of the surgeon. The patient's arms may be held in this position by the straps 40 or using the overlap mode of the device (described hereafter, FIGS. 6 and 13). While arm is in said wrapped engagement, minimal movement of said arm is permitted. Foot securement restraint 13 is also engaged. The present invention positions and secures patient 20 during transfer preventing injury to the patient and hospital staff when dragging the device 10 by handles 14. Furthermore, the patient is now more easily transferable between one support surface to another, for example, a gurney to an operating table. The handles 14, engaged around the perimeter of the overhang sections 11, provide personnel a secure grip while sliding or lifting a patient from one surface to another.

Figure 6:
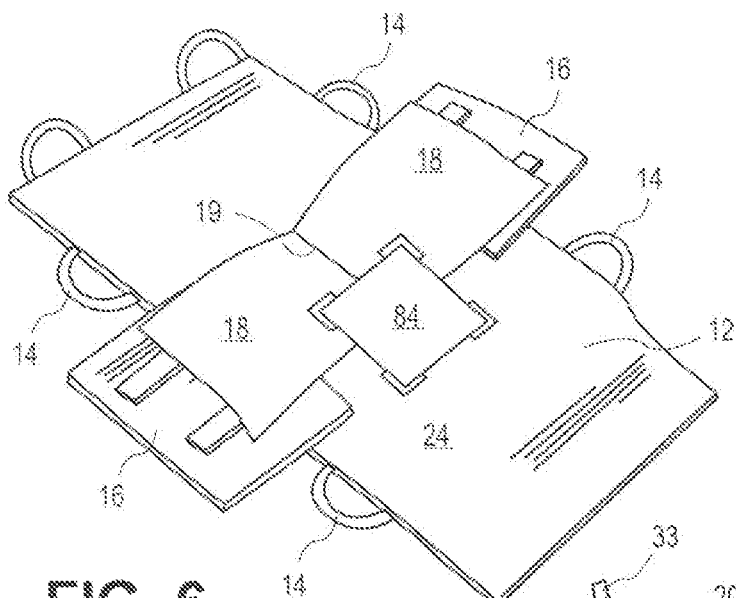
FIG. 6 depicts one embodiment of the device with a foam pad removably engaged.
Figure 13:
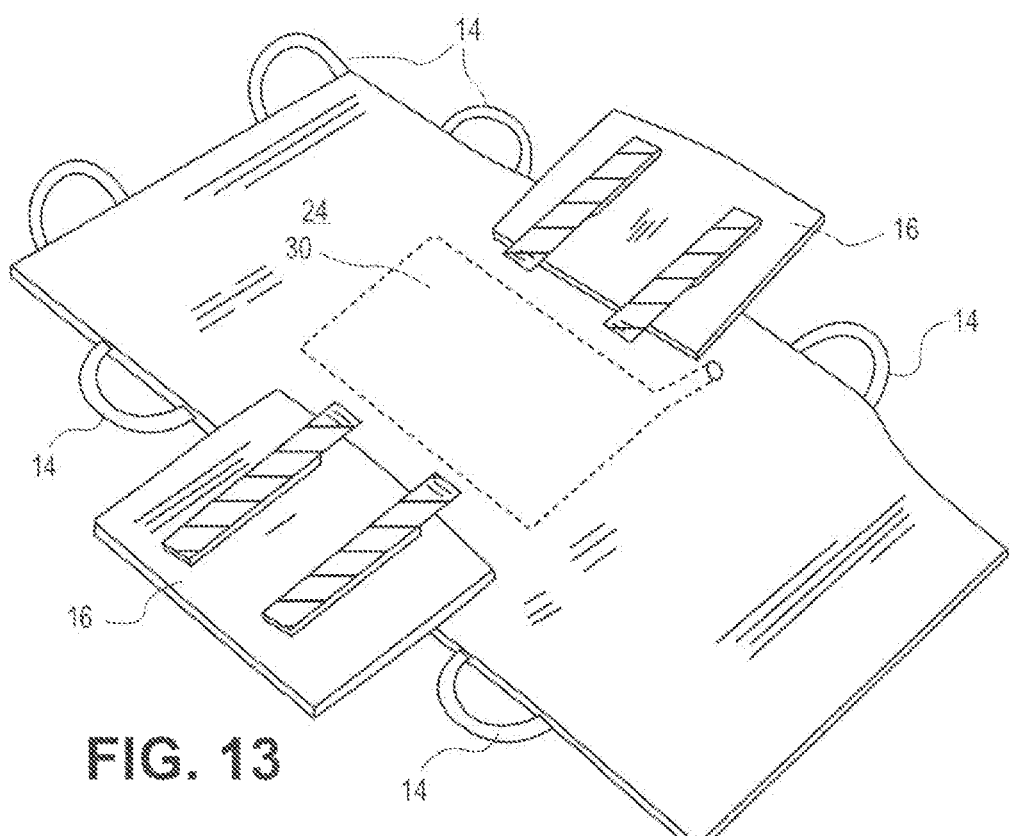
FIG. 13 depicts a top surface view of one embodiment of the device with optional inflatable support.

In an example embodiment of the invention, an overlap system may be employed to further secure and elevate the patient's arms. The overlap system employs flexible, rectangular overlap substrates 18 oriented lengthwise across the width of the center section 12 and attached at the centerline 19 as depicted in FIGS. 6 and 13. The bottom surface of the overlap substrates 18 have strips of hook and loop fasteners 44 which fasten to the hook and loop fasteners on the padded substrates 16 when engaged. The overlap substrates 18 provide a secondary means to secure the patient's arms and as noted and shown in FIGS. 11 and 12, the overlap substrates 18 are tucked under a pad or mattress.

FIG. 6 shows the device 10 as optionally having a soft, foam pad 84 removably engaged to the top surface 24. This foam pad 84 is strategically placed in the buttock area to prevent pressure ulcers that may occur when a patient remains in the same position for an extended period of time such as during a long surgery or when a patient is confined to a hospital bed. Engagement may be by peel and stick adhesive or hook and loop fabric, or other means for removable engagement.

Figure 7:
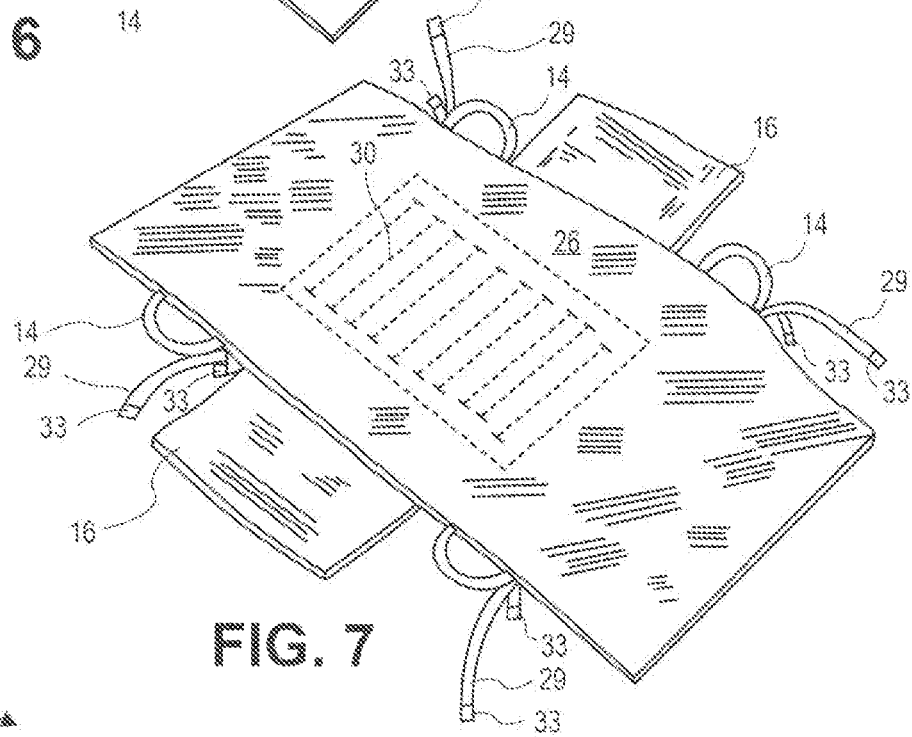
FIG. 7 depicts a bottom view of one embodiment of the device with an optional inflation support.

FIG. 7 shows a view of the bottom surface 26 of the device 10. Belt 29 has connector 33 attached at the respective ends and is coupled to handles 14. This belt 29 and connector 33 secure device 10 to the support surface, for example, an operating table or bed. The quantity and orientation of belt 29 and connector 33 is not limited by the drawing as shown but is merely simplified for illustrative purposes.

The bottom surface 26 is constructed of a slippery fabric such as vinyl or Teflon coated fabric or another fabric which has a low coefficient of friction. The slippery fabric provides a means to aid in sliding the patient 20 in transitions. Also, a dotted line outline is depicted illustrating the position of an optional inflation support 30. This inflation support 30 is sandwiched between the top surface 24 and bottom surface 26 surfaces and when inflated, allows for an easier sliding of the patient 20.

Figure 8:
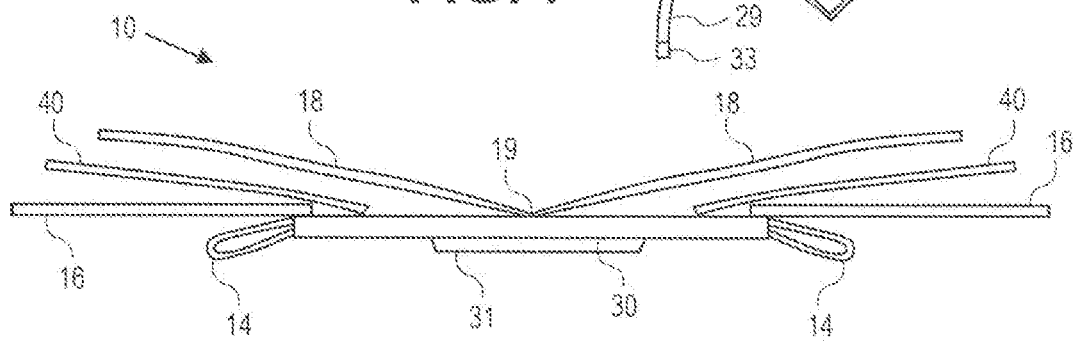
FIG. 8 depicts a cut through view of one embodiment of the device ready for a patient and to be placed in an as-used position.

FIG. 8 shows a cut through view of the device 10 ready for a patient 20 and to be placed in an as-used position as noted in the following figures, FIGS. 9-12. FIG. 9 depicts an end view of the as-used position of an example of the device 10 prior to engagement of the padded arm restraints provided by the padded substrates 16. In use, the padded substrates 16 encircle the arm of the patient 20, and are then secured by straps 40 having hook and loop fasteners or other means of engagement.

Figure 14:
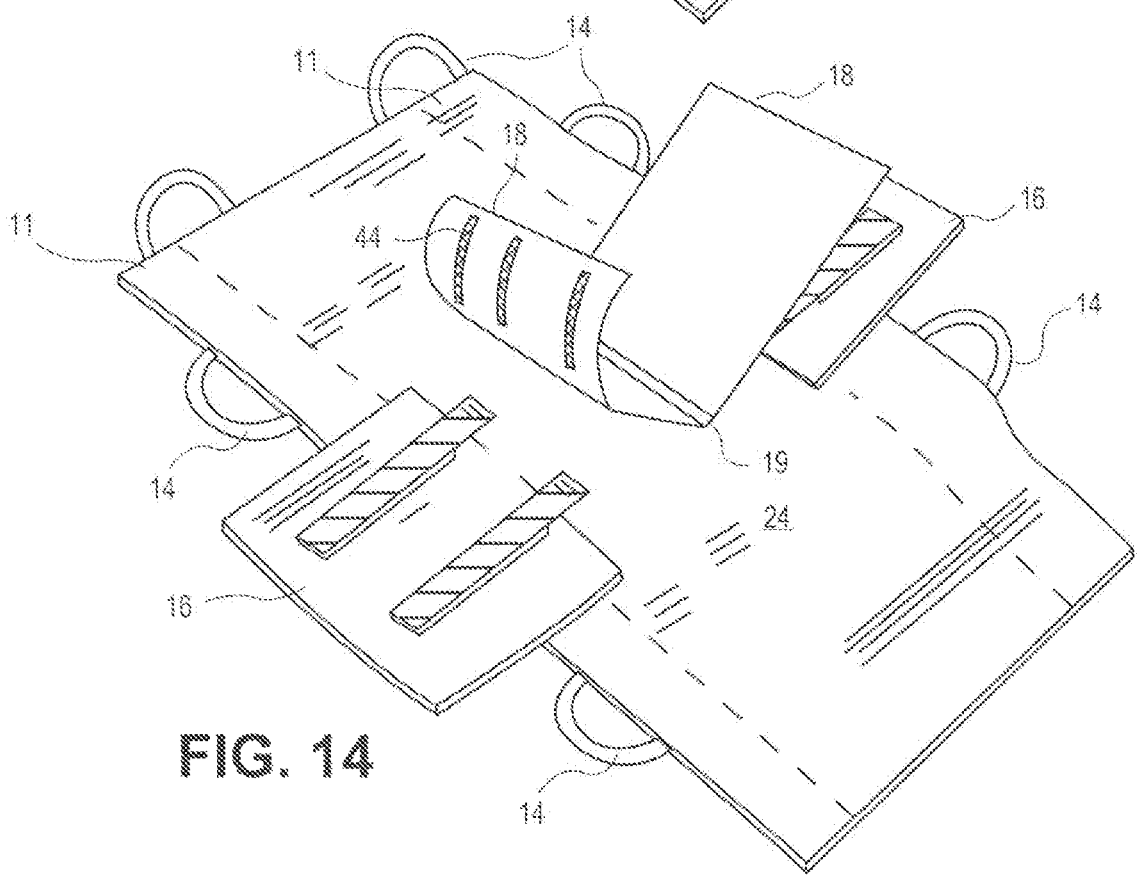
FIG. 14 depicts one embodiment of the device with the padded substrates, overlap substrates, and formed inflated members.

Referring to FIG. 10, the padded substrates 16 encircle the patient's arms and are secured by straps 40 which comfortably hold the patient's arms close to the body. Additionally, the arms are padded and protected from injury from laying on the support surface too long or from the pressure of the surgeon's weight. Also, with the padded substrates 16 so engaged, it provides a means to elevate the arms a distance "E" above the support surface. This helps prevent nerve damage and tissue damage caused by an arm sitting on a surface too long during surgery. FIGS. 11-12 show the engagement of overlap substrates 18 which may be wrapped over the patient's arms and tucked under the pad or mattress of the gurney or operating table. This provides secure positioning of the patient for surgery or transport. FIG. 13 depicts another top surface view of one embodiment of the present device and FIG. 14 shows the device with the padded substrates, overlap substrates is a disengaged position.

Figure 15:
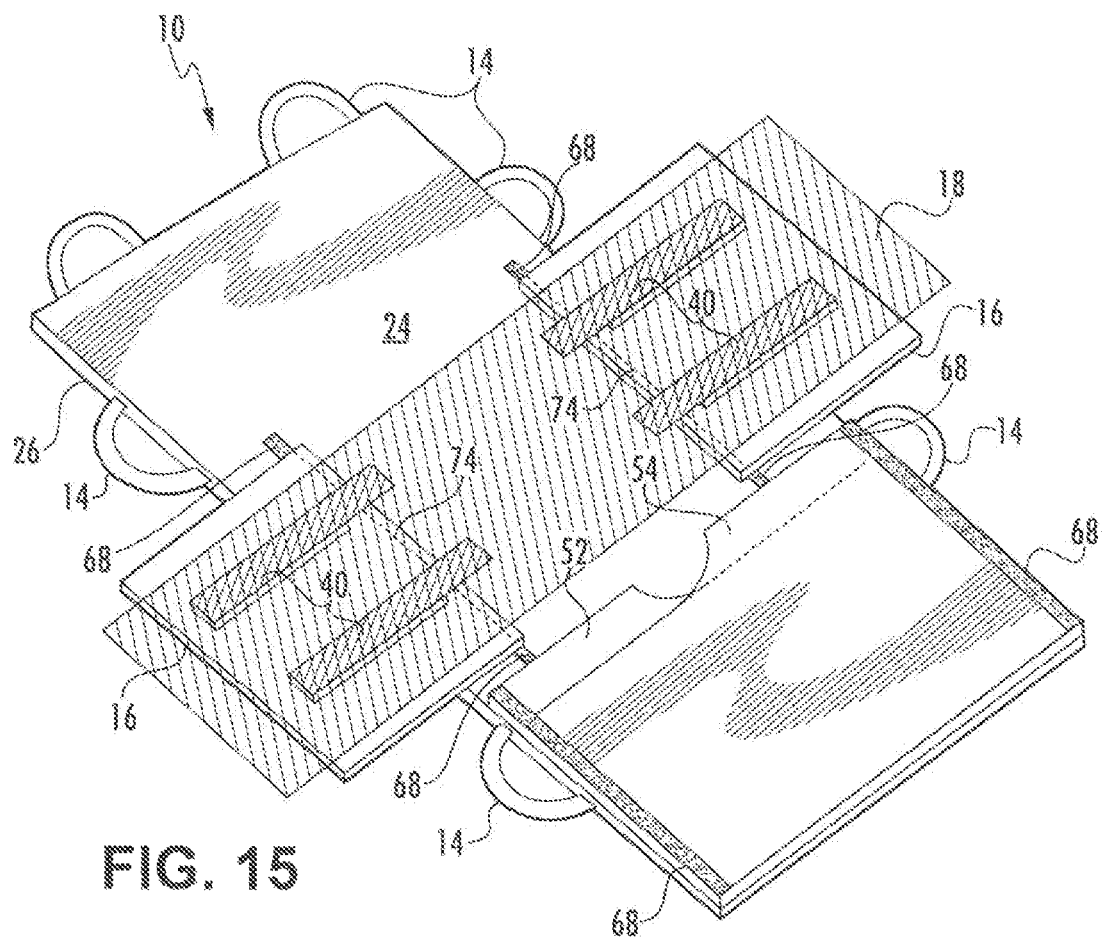
FIG. 15 depicts an embodiment of the patient positioning device.

FIG. 15 depicts another embodiment of the patient positioning device 10. A top surface 24 is positioned opposite a bottom surface 26. Top surface 24 and bottom surface 26 are formed of a flexible fabric sheet. A center section is of a rectangular geometry and adapted in length and width to accommodate the size and shape of a human being. A plurality of handles 14 are coupled to the outer edge of the sheet which allow for a safe grip on the device when used for lifting, pulling or moving the device while the patient is being supported by top surface and secured. The quantity and orientation of handles 14 is not limited by the figure as shown but is merely simplified for illustrative purposes. Bottom surface 26 which is exposed, may be formed of any low friction material as would occur to those skilled in the art including but not limited to one or a combination of materials from a group including PTFE impregnated or coated fabric, spunbond or other fabric when woven or formed has a slippery surface, or fabrics such as rip-stop or micro fiber-based materials woven or knitted from woven nylon, or polyester. The slippery bottom surface 26 may be sewn or laminated or coated to device 10 or on the opposite side of the material forming top surface 24.

FIG. 15 also shows two disengaged padded substrates 16 which have a layer of padding imbedded or engaged such that when engaged around the arm of a patient, a means to pad the arm is provided. This protects the patient's arm from any pressure forces imparted by the table or by a surgeon. Padded substrates 16 also are configured to engage around the arms of the patient, and hold them against their body and slightly elevated from the underlying table or support surface. This helps eliminate injury to the patient's arm when it is supported on a hard table surface for a long duration by placing a gap between the table and arm.

The back surfaces of padded substrates 16 have strips of hook and loop fasteners for securing. Straps 40 have hook and loop fasteners for securing to padded substrates 16 when padded substrates 16 are wrapped around a patient's arm. In an example embodiment of the invention, an overlap system may be employed to further secure and elevate the patient's arms. The overlap system employs a flexible, rectangular overlap substrate 18 oriented lengthwise across the width of top surface 24 and attached to top surface 24. The bottom surface of overlap substrate 18 has strips of hook and loop fasteners which fasten to the hook and loop fasteners on the padded substrates 16 when engaged. Overlap substrate 18 provides a secondary means to secure the patient's arms. The functionality here is substantially shown and described above in FIGS. 9-12. Furthermore, in some embodiments, the device 10 includes a first and second flexible substrate forming legging 52 and legging 54.

Figure 16A:
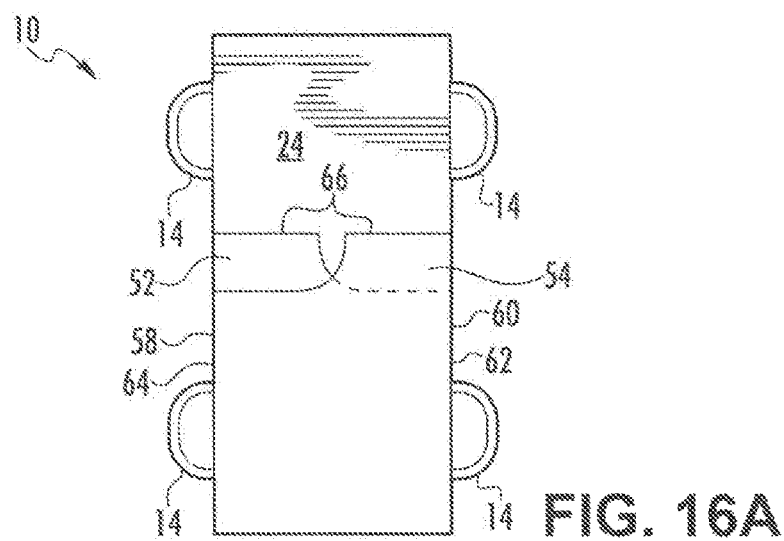
FIG. 16A depicts an embodiment of the patient positioning device.

FIG. 16A depicts another embodiment of the patient positioning device. This embodiment is simpler than the embodiment of FIG. 15 and focuses on the leg portion. A planar sheet has a first and second side edge and a top surface 24. This sheet is configured for positioning a patient thereon where the patient is supported by top surface 24 with the first and second side edges adjacent to the legs of the patient. A first and second flexible substrate capable of wrapping around an adjacent leg of a patient, thus creating a wrapped engagement, are detailed as legging 52 and legging 54. These wrapped engagements of the legs prevent heat loss during pre-surgery, surgery, post-surgery or transport and protect against pressure injury.

Legging 52 is mostly covered by legging 54 until it is engaged with the patient's leg. For example, more than 50%, 60%, 70%, 75%, 80%, 90% or 95% of legging 52 may be covered by legging 54. Referring to FIGS. 15 and 16A, to use the patient positioning device in one embodiment, the patient is positioned on top surface 24. Optional padded substrates 16 are configured to engage around the arms of the patient, and hold them against their body and slightly elevated from the underlying table or support surface. This helps eliminate injury to the patient's arm when it is supported on a hard table surface for a long duration by placing a gap between the table and arm. Padded substrates 16 are wrapped around a patient's arms and secured with strips of hook and loop fasteners and straps as described above.

Legging 52 and legging 54 are configured to engage around the legs of the patient to protect the patient as well as prevent heat loss. Once the patient is positioned on top surface 24, the user would grasp and lift free edge 64 (see FIG. 16A) of legging 54 wrapping this flexible substrate around, e.g., over and then under, the adjacent leg, creating a wrapped engagement (see FIG. 17). Fasteners such as hooks of a hook and loop (e.g., Velcro®) may be located on the underside of legging 52 and legging 54 at respective free edges 62 and 64 (see FIG. 3A) while loops from a hook and loop fastener (e.g., Velcro®) may be located on the topside of legging 52 and legging 54 at respective attached outer edges 58 and 60 (see FIG. 3A).

Figure 16B:
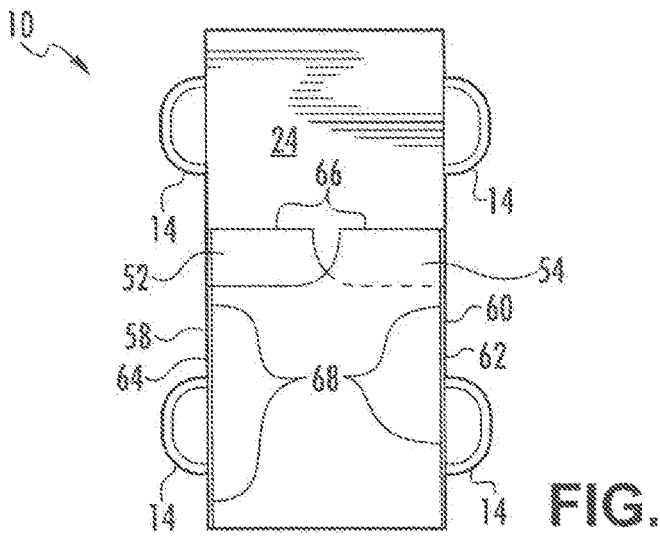
FIG. 16B depicts an embodiment of the patient positioning device with continuous attachment points.
Figure 16C:
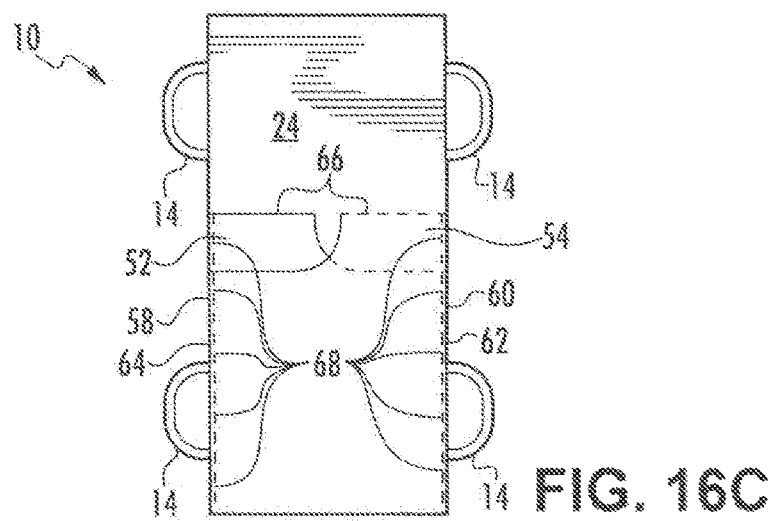
FIG. 16C depicts an embodiment of the patient positioning device with non-continuous attachment points.
Figure 16D:
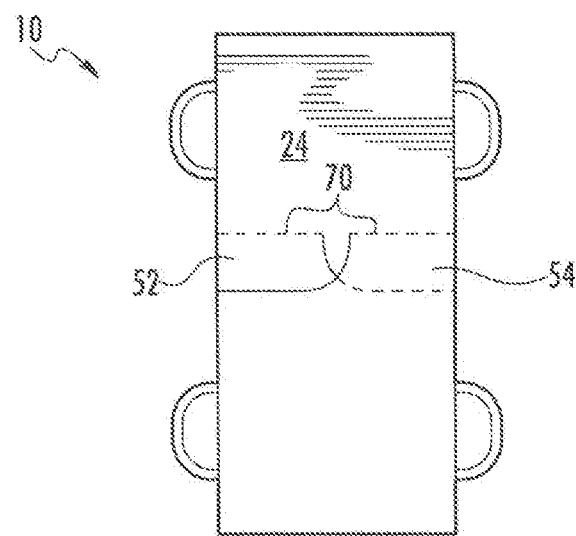
FIG. 16D depicts an embodiment of the patent positioning device with perforated and disposable leggings.

Referring to FIG. 16A, the lower portion of top surface 24 is the area of attachment for legging 52 and legging 54. These are substantially planar and integral with the sheet and attached at a top edge 66 of legging 52 and legging 54 to top surface 24. Legging 52 is also attached at an outer edge 58 of top surface 24 while legging 54 is attached at an outer edge 60 of top surface 24. These attachment areas 68 may be continuous along the entire outer edge as shown in FIG. 16B or may be non-continuous as shown in FIG. 16C. Also, the attachments may be permanently attached such as by sewing, or temporarily attached such as by hook and loop fastener (e.g. Velcro®) allowing adjustability. In one embodiment, legging 52 and legging 54 may be constructed from a material that is perforated 70 and disposable. In this way, the leggings may be easily, conveniently and completely removed from top surface 24 and thrown away. FIG. 16D illustrates this embodiment.

Figure 17:
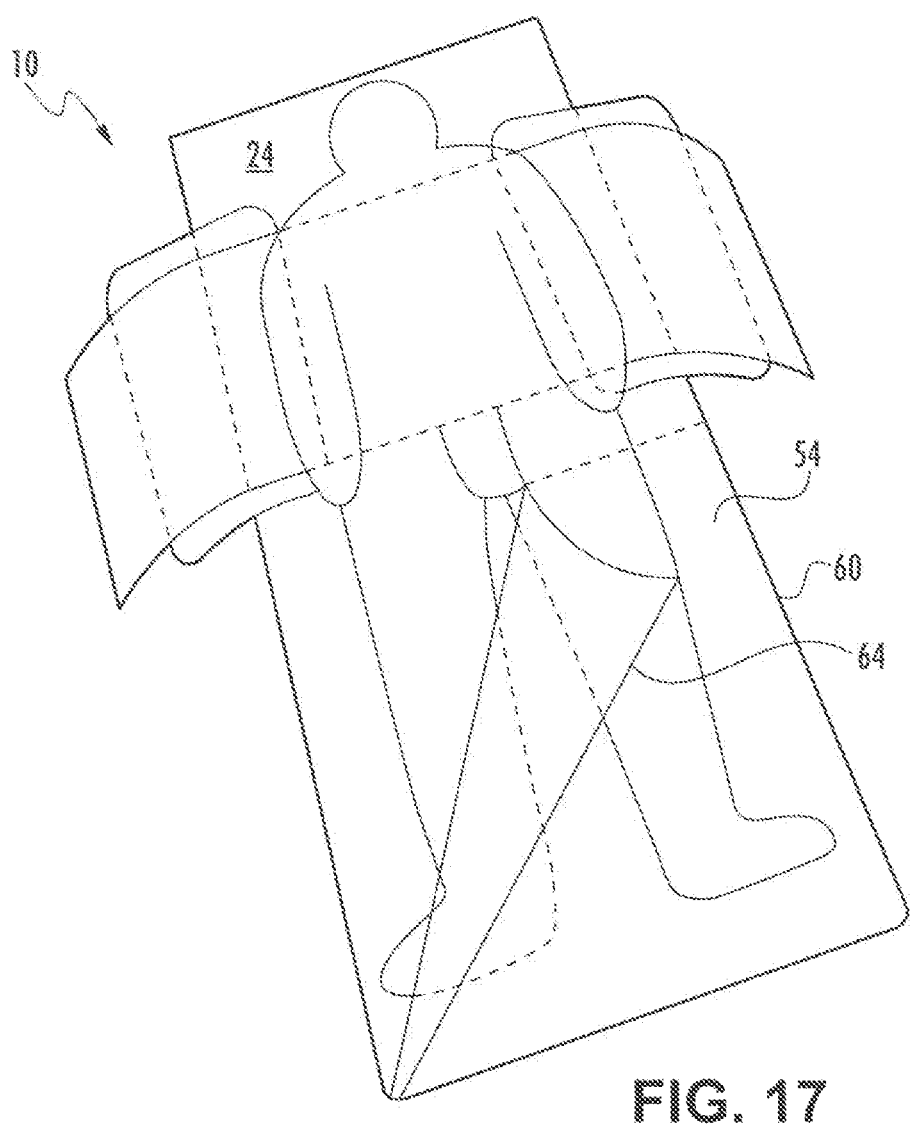
FIG. 17 depicts an embodiment of the patent positioning device with a patient supported thereon.

FIG. 17 illustrates an embodiment of the present invention with a patient supported thereon. The patient positioning device 10 is utilized to position, protect and secure a patient on a support surface for transfer to another support surface or for preparation for surgery. In different embodiments, it may function as a regular bed sheet, a surgical bed sheet, leggings or any combination. To utilize the legging feature, after the patient is positioned and secured on the sheet, legging 52 and legging 54 may be engaged. To do this, an unattached edge, or free edge 64 of legging 54 is lifted and wrapped around, i.e., over and then under, the adjacent leg, and then fastened. Legging 52 is constructed in the same manner but using free edge 62 of legging 52.

Figure 18:
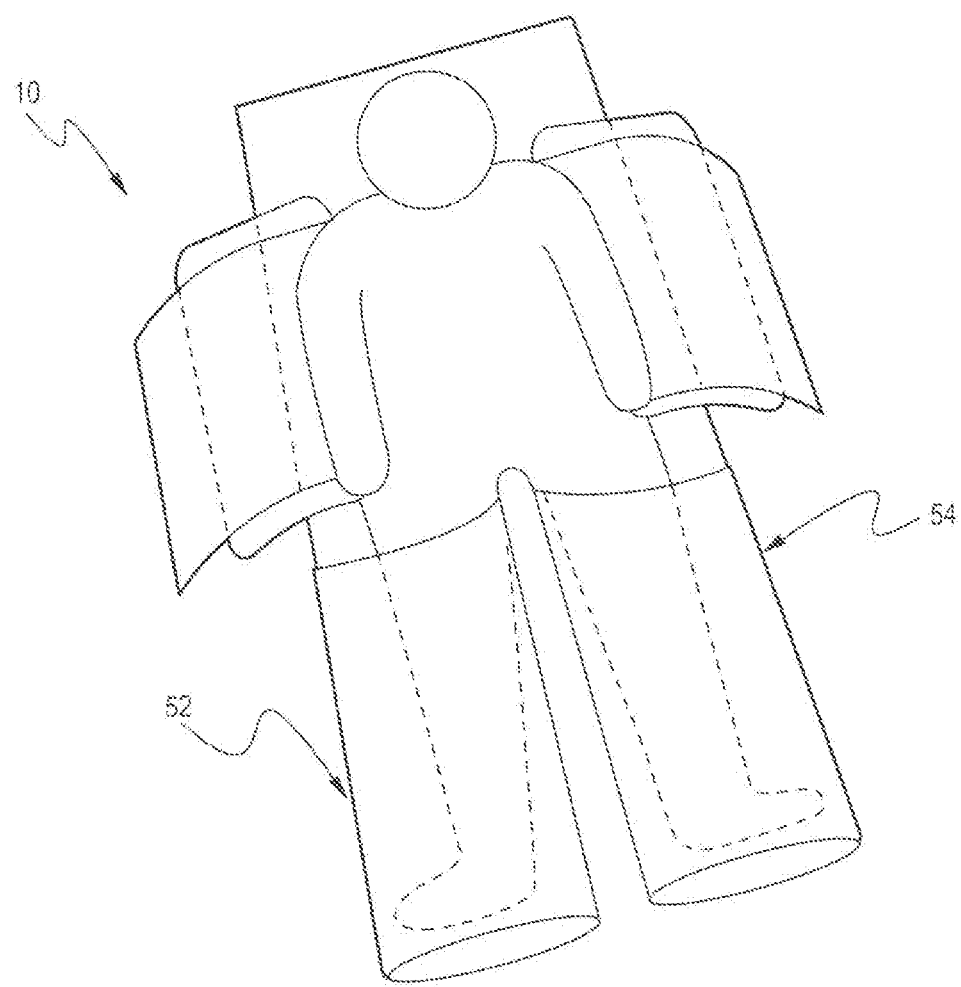
FIG. 18 depicts an embodiment of the patient positioning device with the legging wrapped engagements.

FIG. 18 illustrates another embodiment of the patient positioning device with the legging wrapped engagements. In this embodiment, legging 52 and legging 54 are loosely fitted on the legs of the patient. In this manner, any necessary medical devices such as leg compression devices, could be used when legging 52 and legging 54 are engaged.

Figure 19:
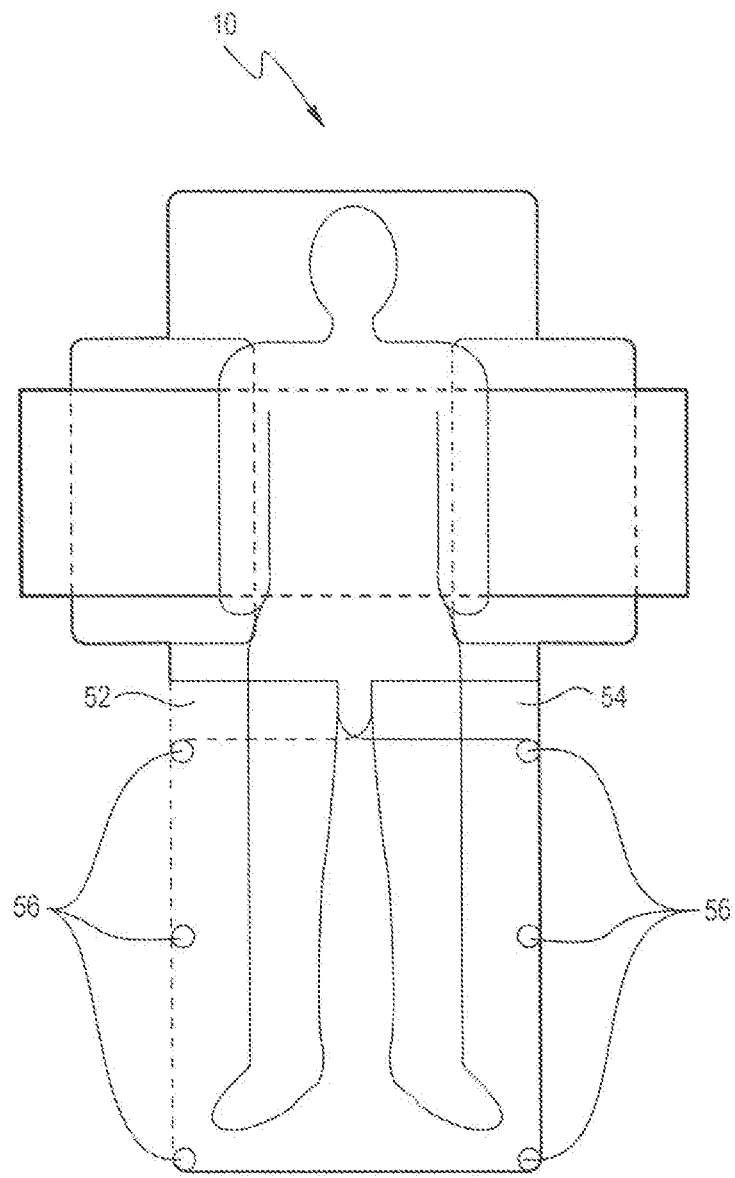
FIG. 19 depicts an embodiment for fasteners for the patient positioning device.

With reference to FIG. 19, to fasten legging 52 and legging 54, fasteners 56 such as hooks from a hook and loop fastener large or small (e.g., Velcro®) are located on the underside of legging 52 and legging 54 at respective free edges 62 and 64 while loops from a hook and loop fastener (e.g., Velcro®) are located on the topside of legging 52 and legging 54 at respective attached outer edges 58 and 60. Fasteners 56 are accessible when respective legging 52 and legging 54 are in the wrapped engagement with a respective leg. FIG. 19 depicts an embodiment for fasteners for the patient positioning device showing a plurality of fasteners. The quantity and orientation of fasteners 56 is not limited by the figure as shown but is merely simplified for illustrative purposes. In one embodiment, fasteners 56 are non-continuous. This allows access to the leg of the patient for medical equipment such as cables and tubes or for monitoring.

Figure 20:
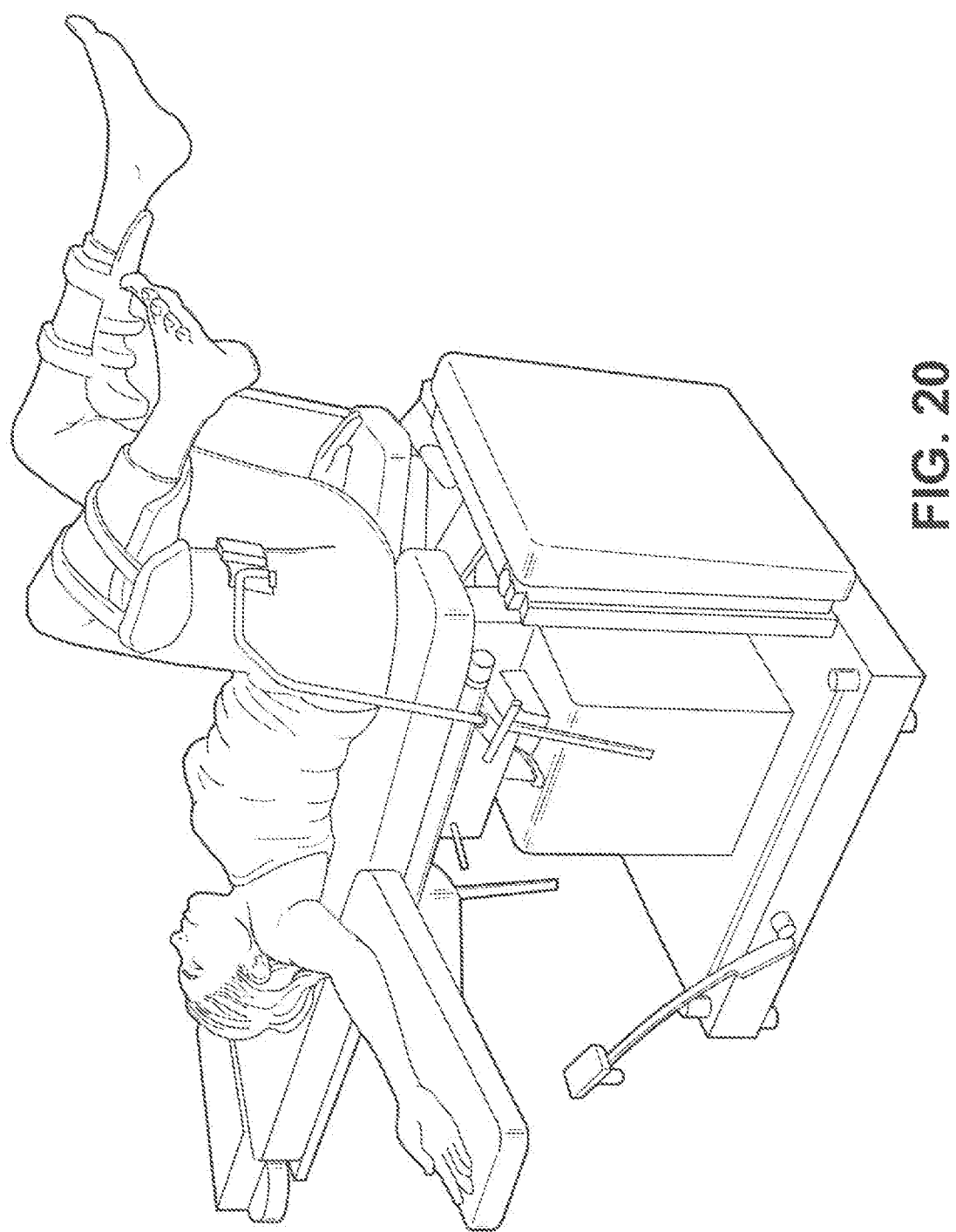
FIG. 20 depicts a patient in a lithotomy position wherein the present invention is particularly useful.

The use of these leggings 52 and 54 is practical when the patient is in a lithotomy position (i.e. when the legs are placed in stirrups, see FIG. 20) thus involving the pelvis and lower abdomen such as during colon or genitourinary surgery. In some embodiments, legging 52 and legging 54 may be padded for protection from pressure injury that may occur due to the medical devices such as stirrups. Some studies have found a significant relationship between prolonged surgical procedures with the patient in the lithotomy position and a circulatory complication. This condition occurs when increased tissue pressure within a limited tissue space compromises the circulation and function of the contents of the space. Nerve injury to the femoral or peroneal nerve is also possible. Padding may be imbedded or engaged in the entire legging 52 and legging 54 or only in certain areas, such as in the area of contact to the knee joint, calf and/or ankle.

Figure 21:
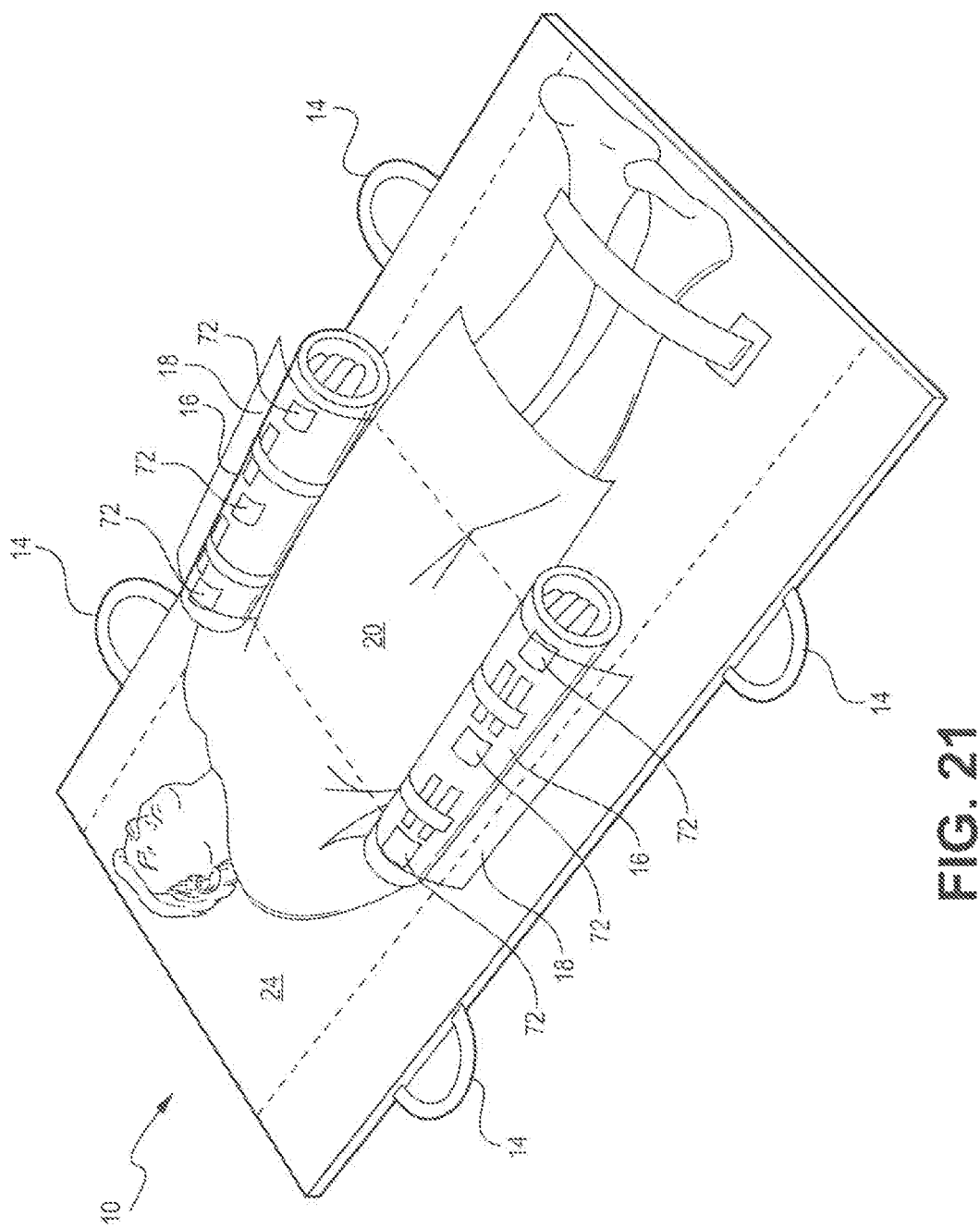
FIG. 21 depicts an embodiment for the patient positioning device with windows on the wrapped engagements for attached devices and viewing the patient's arm.

FIG. 21 shows optional windows 72 on padded substrates 16. Windows 72 in the padded substrates 16, which wrap around a patient's arms, are created for the purpose of passing through medical lines such as blood pressure cuff tubing, pulse-oximeter cables, and/or intravenous lines. These windows are also used for viewing the patient's arm without having to unwrap padded substrates 16 from the patient's arms. In one embodiment, window 72 are openings in padded substrates 16. In another embodiment, window 72 consists of a flap of material attached permanently on one side. In yet a further embodiment, window 72 consists of a flap of material temporarily attached on one or more sides such as with hook/loop Velcro®. The number, configuration, and location of windows 72 may vary and the number shown in FIG. 21 is for illustration purposes.

It is appreciated that in some embodiments, the initial position of legging 52 and legging 54 before the wrapped engagement is flat to top surface 24 as shown in FIG. 15. Referring back to FIG. 15, the position of padded substrates 16 for the patient's arms, along with legging 52 and legging 54 for the patient's legs, may be adjustable by using attachment areas 68, for example, hook/loop Velcro® placement on top surface 24. This allows the device to accommodate a wide range of different patient sizes. Also, padded substrates 16 for the patient's arms may be perforated 74. In this way, the padded substrates 16 may be easily, conveniently and completely removed from top surface 24 for disposal should they become soiled or otherwise need to be disposed of.

Figure 22:
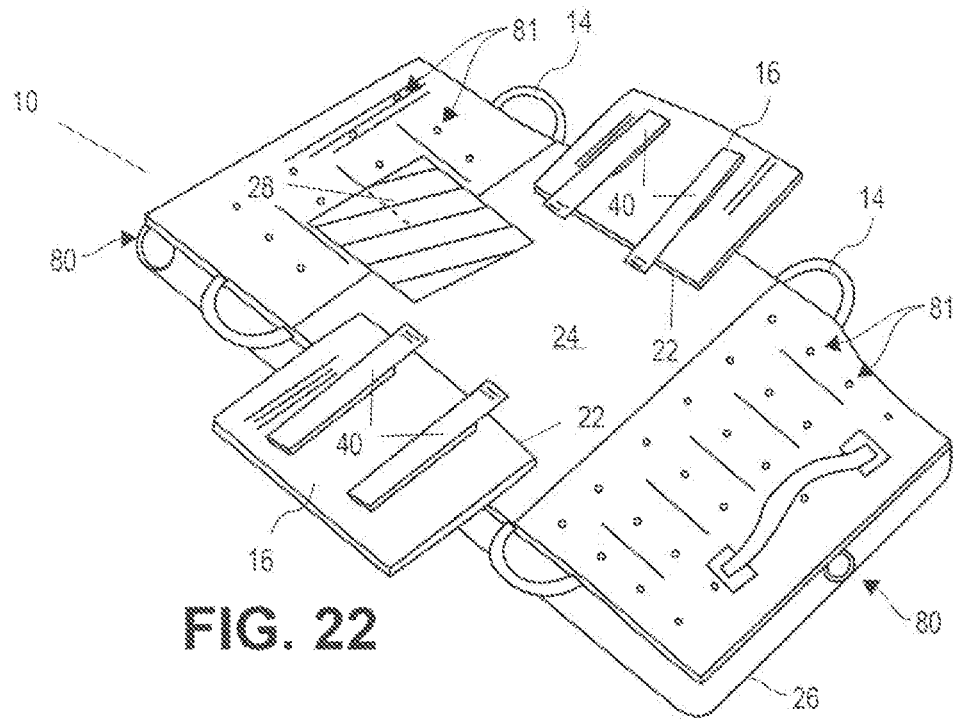
FIG. 22 depicts one embodiment of the device of the present invention including forced warm-air technology.
Figure 23:
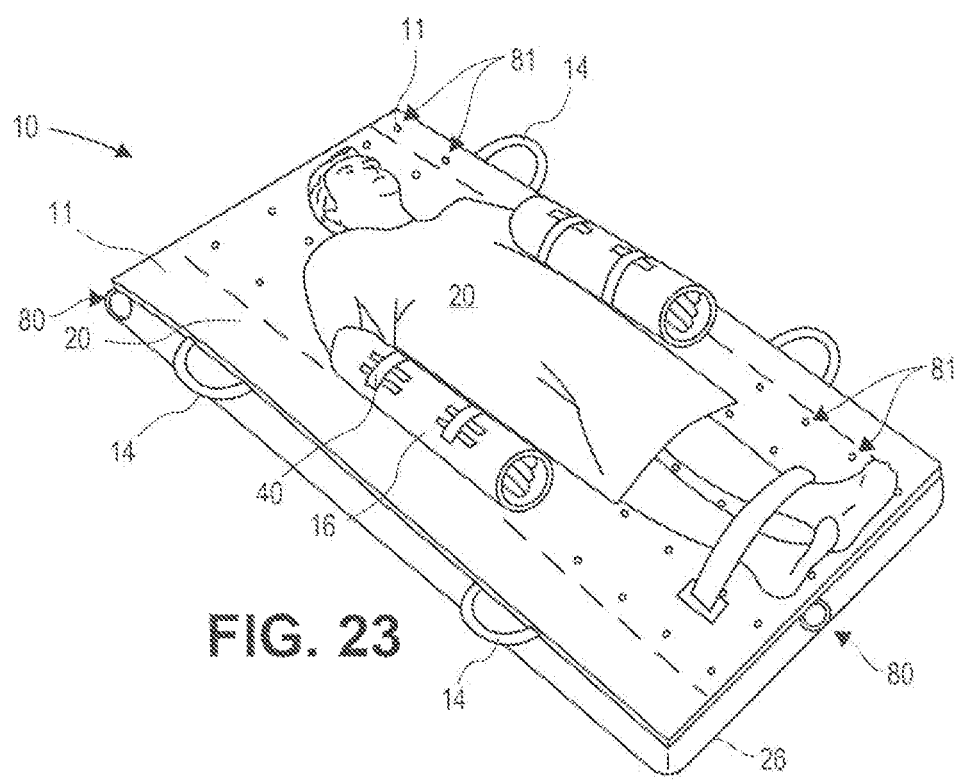
FIG. 23 depicts another embodiment of the device of the present invention including forced warm-air technology.

In some embodiments, forced warm-air technology may be utilized with the present invention. This forced warm-air feature may utilized for the upper portion of the device to provide warmth to the upper extremities. In other embodiments, it may be used for the lower portion of the patient positioning device when configured with legging 52 and legging 54. In some embodiments, both upper and lower portions of the device may be provided with force warm-air features. With reference to FIGS. 22-23 shown is device 10 having forced warm-air capability. In some embodiments, the top and bottom surfaces 24 and 26 define a flexible bladder-type sheet which includes an inner space configured to receive forced warm air. In some embodiments, one or more warm-air inlets 80 are provided. As shown in FIG. 22, a warm-air inlet 80 is provided at the upper portion as well as the lower portion 10 of the device. The inlet 80 is configured to receive a hose or tubing from a forced warm-air machine such as a compressor or the like that provides a warm air source. The top surface 24 of the device 10 includes a plurality of apertures 81 through which the warm air flows. The air flows into the inlets 80 and out of the apertures 81 thus providing warm air around all or a portion of the patient as shown in FIG. 23. In the warm-air application, the bottom layer 26 which is made out of low friction nylon material or similar and is airproof and waterproof. The top layer 24 is preferably made out of Polypropylene material or similar for patient comfort. Through this top layer, a plurality of pinpoint holes 81 are created for warm air to escape and come into contact with the patient's skin as a means of warming the patient or maintaining the patient's temperature during surgery.

In other embodiments, the apertures 81 may be placed in legging 52 and legging 54 to allow forced warm-air to penetrate through the openings and onto the patient's skin. In this manner, using forced warm-air may warm the patient or may help maintain body temperature thus preventing hypothermia. Also, a blanket may no longer be required when using the device because legging 52 and legging 54 may provide the warming function.

Figure 24:
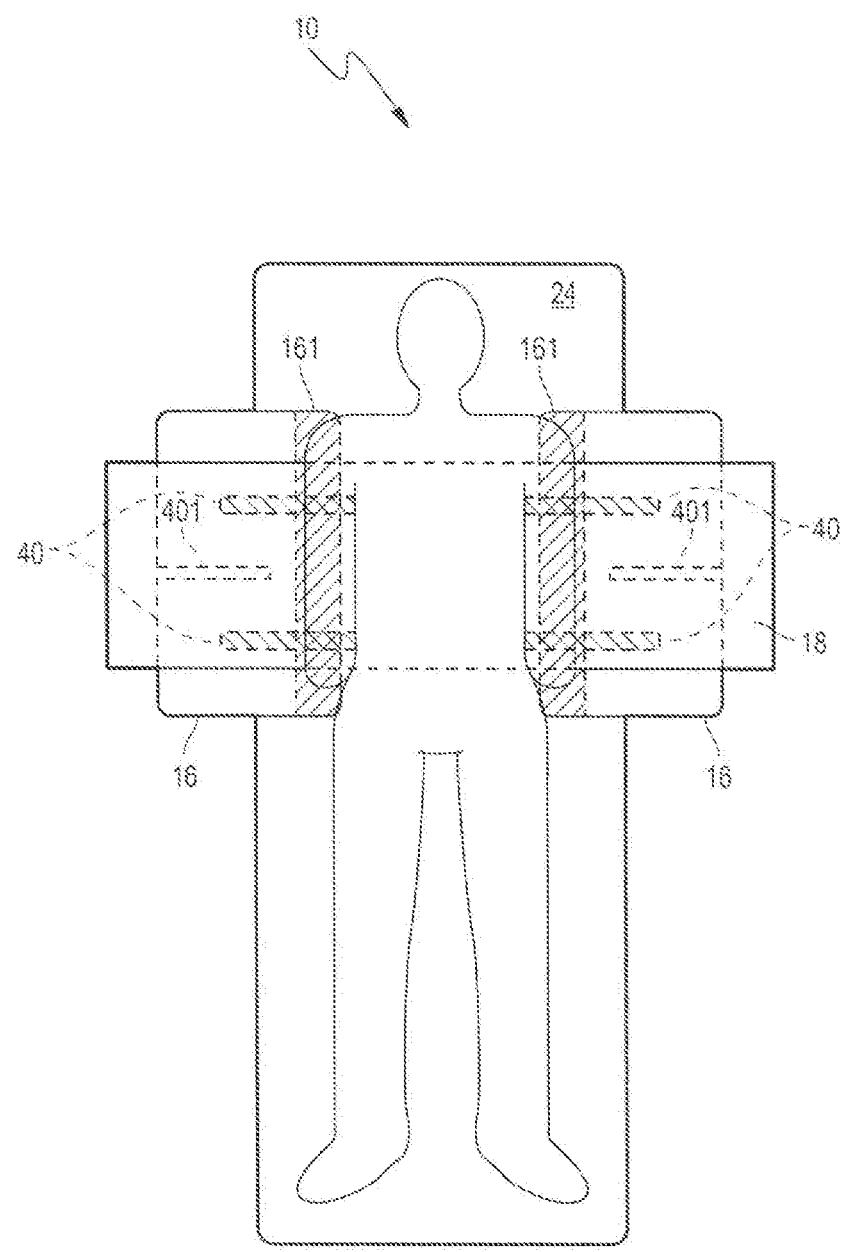
FIG. 24 depicts one embodiment of the device of the present invention including an alternative design of the padded substrates.
Figure 25:
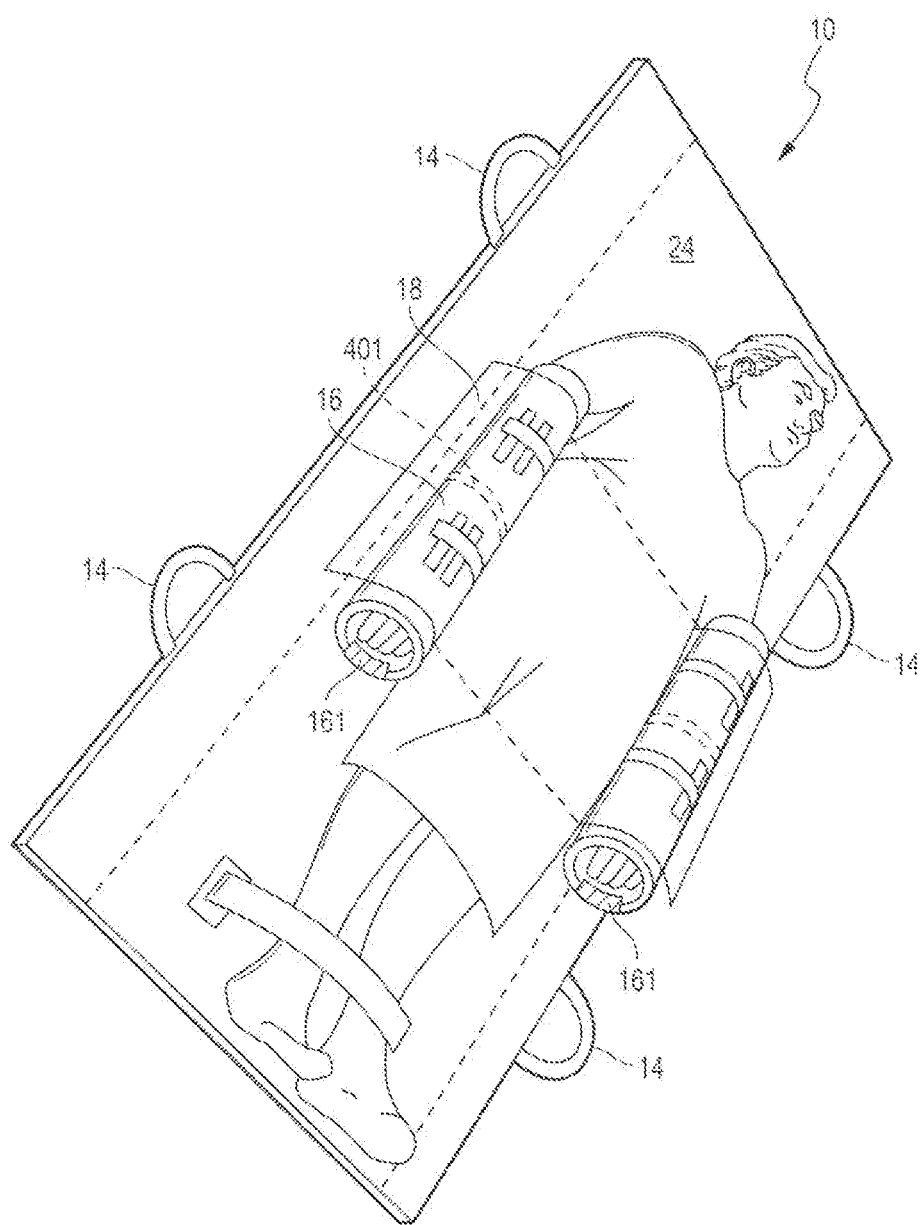
FIG. 25 depicts another embodiment of the device of the present invention including an alternative design of the padded substrates.

With reference to FIGS. 24 and 25, in some embodiments, the padded substrates 16 are configured to conform to the arms of patients of various sizes and shapes. FIG. 24 illustrates the device 10 with the patient positioned with both arms disposed above padded substrates 16 where the substrates are disengaged. In some embodiments, padded substrates 16 include additional padded sections 161 which are preferably aligned with the gravity dependant section of the patient's arms. In other words, the additional padded sections 161 are preferable disposed directly beneath the patient's arms, between the arm and the underlying support structure. With reference to FIG. 25, the patient is positioned on the patient positioning device and straps are employable to hold the flexible, padded substrates 16 in wrapped configuration around the patient's arms and maintain the arms close to their body and out of the way of the surgeon. The patient's arms may be held in this position by the straps or using the overlap mode of the device (described above, FIGS. 6 and 14). While the arm is in the wrapped engagement using two straps 40, minimal movement of the arm is permitted. Further, the wrapped engagement is configured to elevate the arm or arms above the support surface to prevent pressure injury and nerve damage.

With reference again to FIGS. 24 and 25, to further adapt the substrates 16 to a variety of sized and shaped arms, a split 401 is provided transversely across substrates 16 which birfurcate at least a portion of the substrates. In some embodiments, this split 401 allows the padded substrate 16 to conform around larger arms or an arm that may already be in a protective brace, splint, or cast. Further, the split 401 on the padded substrates 16 allow for the routing of wires, cables, and I.V. lines. In some embodiments, the wire, cable and I.V. lines can extend from the patient's hand/arm and be secured/organized between the padded substrate 16 and the overlap substrate 18. This will prevent the wire, cable and I.V lines from "hanging loose" at the side of the operating table and become detached or tangled. The split 401 in combination with the additional padded sections 161 provide additional comfort and security for both the patient and hospital workers.

Figure 26:
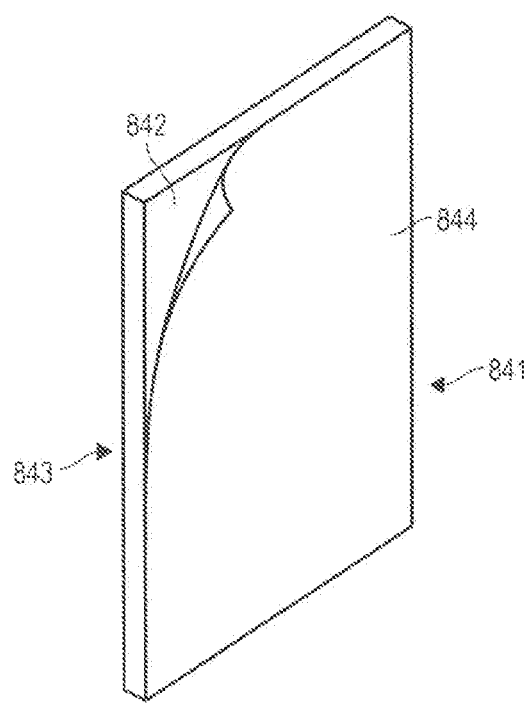
FIG. 26 depicts one embodiment of a dual-sticky pad accessory for the device of the present invention.
Figure 27:
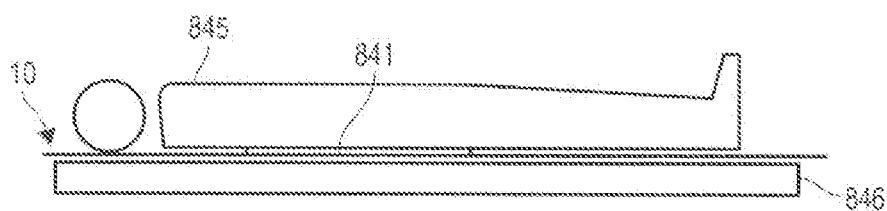
FIG. 27 depicts one embodiment of the dual-sticky pad in use with the device of the present invention in a horizontal position.
Figure 28:
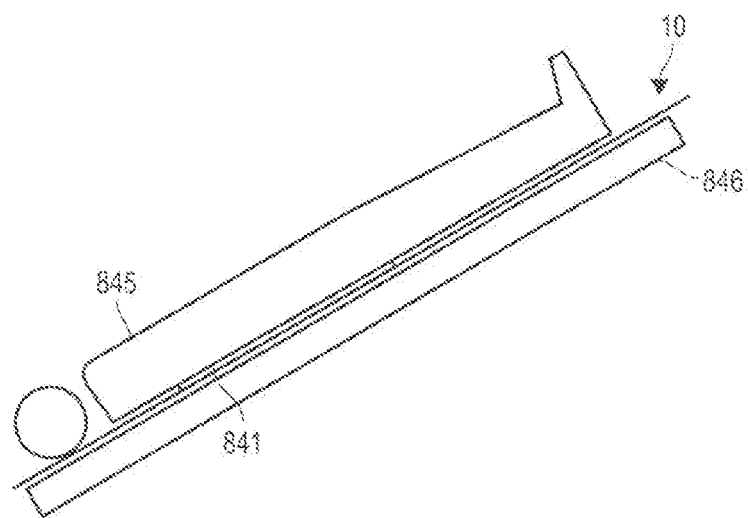
FIG. 28 depicts a embodiment of the dual-sticky pad in use with the device of the present invention in a Trendelenburg position.
Figure 29:
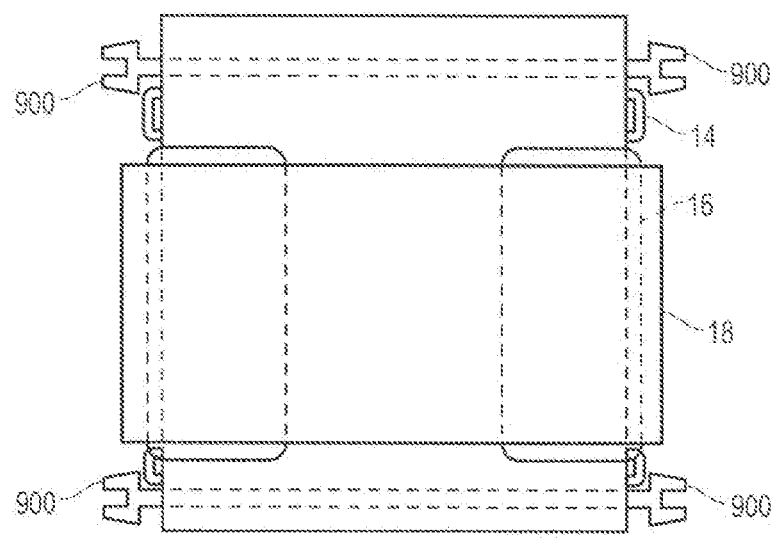
FIG. 29 depicts another embodiment of the patient positioning device of the present invention adapted for use when a patient is to be in a prone position.
Figure 30:
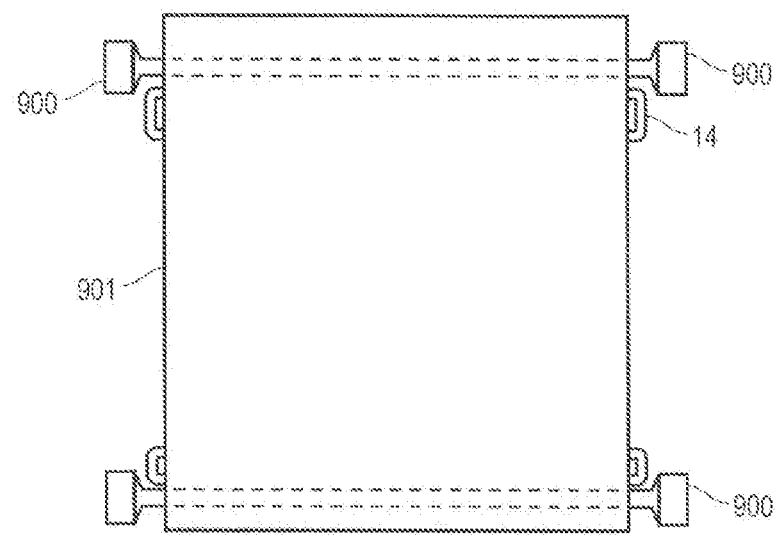
FIG. 30 depicts one embodiment of a secondary sheet that is used in conjunction with the patient positioning device when a patient is to be in a prone position.

During surgery, it is frequently necessary to change the operating table from flat to Trendelenburg position (head down) to optimize the surgical field for the surgeon to perform the necessary surgery, such as during surgery of the prostate, colon, or uterus/ovaries. Accordingly, with reference to FIGS. 26-28, provided as an accessory to the patient positioning device 10 is a dual-sticky pad 841 to use in conjunction with patient positioning device 10 to help secure a patient during surgery while on a support surface to reduce sliding risk when changing positions from flat to Trendelenburg position (head-down) and vice versa. In some embodiments, the dual-sticky pad 841 comprises a generally planar sheet of adhesive material having a first adhesive side 842 and a second adhesive side 843. In some embodiments, a removable backing layer 844 is provided which protects the adhesive during storage. As shown in FIG. 27, the dual-sticky pad 841 is disposed between the patient 845 and the support surface 846. In some embodiments, the dual-sticky pad 841 is placed between the patient's back and the patient positioning device 10 such that they become a single unit. The unit can then be secured to the operating table using the belt 29 and connectors 33 shown in FIG. 7. Thus, the sticky pad 841 prevents the patient, on the device 10, from sliding when the operating table is changed from flat position (0 degree) to Trendelenburg position (head-down), which is shown in FIG. 28.

Figure 31:
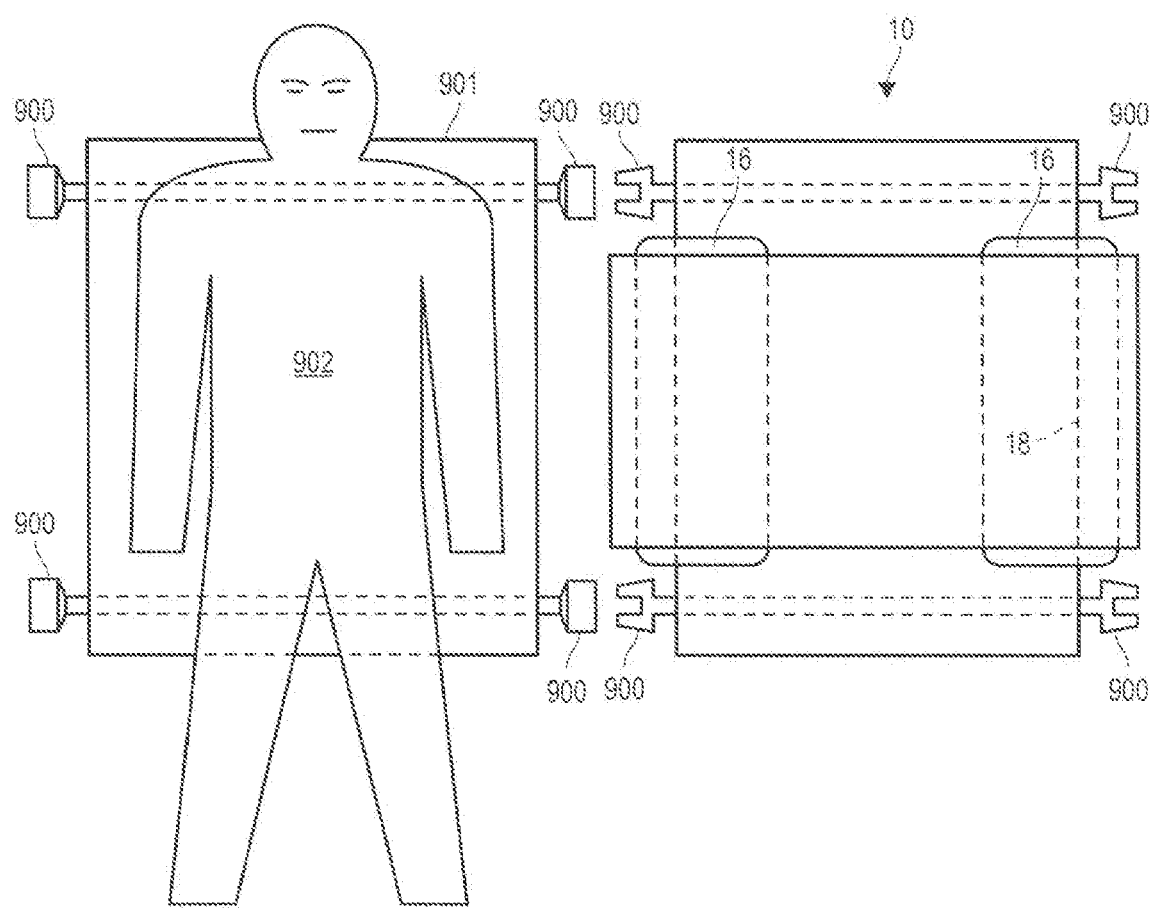
FIG. 31 depicts a top view of the patient positioning device, secondary sheet, and a patient configured for use when the patient is to be in a prone position.
Figure 32:
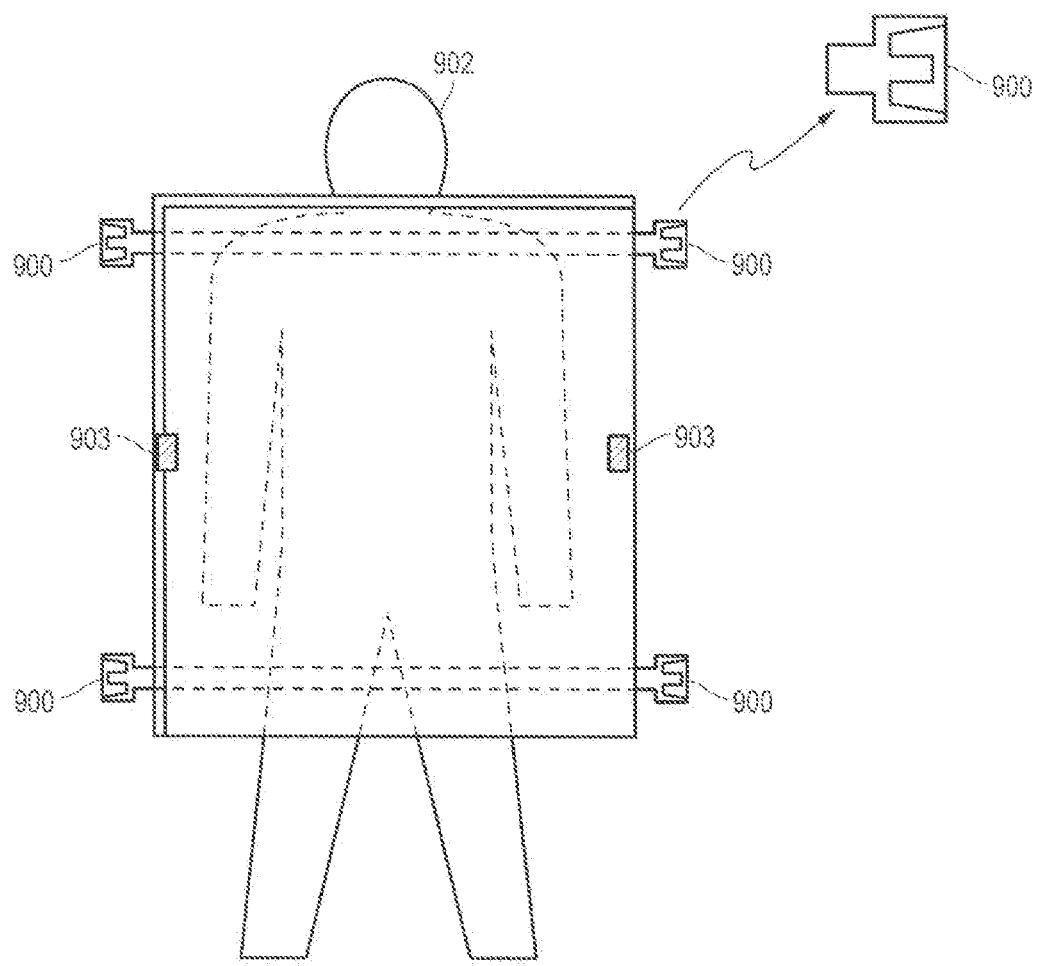
FIG. 32 depicts another top view of the patient positioning device, secondary sheet, and a patient configured for use when the patient is to be in a prone position.
Figure 33:
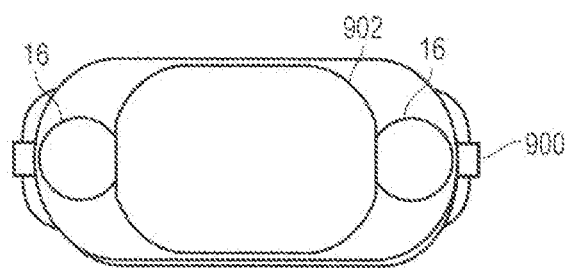
FIG. 33 depicts a cross-sectional view of the patient positioning device, secondary sheet, and a patient configured for use when the patient is in a prone position.

In yet another embodiment of the present invention, additional features are provided to secure and protect a patient who may be oriented in a prone, or face down position. With reference to FIGS. 29-33, a modified patient positioning device 10 is provided, including padded substrates 16 for forming wrapped engagements around a patient's arms for protection and elevation, as well as the overlap substrate 18 for further securement and protection of the patient. One or more handles 14 are attached at the corners of the device 10. Further included are one or more buckles 900 which may be located proximal to the handles at the corners of the device 10. In conjunction with device 10 is a secondary sheet 901 shown in FIG. 30. Secondary sheet 901 is a substantially planar sheet and it some embodiments it matches the dimensions of patient positioning device 10. Secondary sheet 901 includes one or more handles 14 and one or more buckles 900, both disposed toward the corners of the sheet 901. The buckles 900 of the secondary sheet are located and configured to engage the buckles 900 of the device 10. In some embodiments, the buckles 900 of the secondary sheet 900 have male fittings while the buckles 900 of the device 10 have female fittings, allowing for a removable engagement thereof. In other embodiments the buckles 900 of the secondary sheet 900 have female fittings where those of the device 10 have male fittings. With reference to FIG. 31, a patient 902 is disposed with his back on the secondary sheet with the device 10 to be placed on his chest. Optionally, the patient's arms can secured by way of the padded substrates 16 and the overlay substrate 18 as described above. Then the secondary sheet 901 is secured to the device 10 by way of the buckle engagement 900/900 shown in FIG. 32. This configuration forms a "cocoon" around the patient as shown in FIG. 32 wherein the patient is sandwiched between device 10 and secondary sheet 901 with his arms secured by the wrapped engagements of the present invention. This arrangement provides significant protection and security for a patient who must be treated in a prone position as it draws the arms in, elevates them, and then surrounds the entire body is a secure cocoon that prevents dislodgement of the positioning device 10 during movement and repositioning of the patient. This will help secure all the arms/legs, IV access, Foley catheter and any other attachments together prior to positioning change from supine to prone or vice versa.

With this "cocooning", a true "log-roll" technique is provided to ease the process of positioning change as well as preventing injury to the anesthetized patient and the surgical team. For example, the patient, in supine position, has already been placed on the secondary sheet 901 on the gurney as shown in FIG. 31. The device 10 is then placed on top of the patient aligning the buckles 900 securing them together as shown in FIG. 32. The buckles 900 may have adjustable straps which can then be pulled for snug fit. The device 10 and secondary sheet 901 may be further secured using the Velcro attachments 903. After checking all the attachments, i.e. IV accesses, Foley catheter, the patient is ready to be repositioned to prone position. The gurney with the anesthetized patient is now placed side-by-side with the operating table for the repositioning. The whole surgical team must be present for this repositioning procedure as each person on the team is assigned a specific task to avoid injury to the anesthetized patient, i.e. the anesthesiologist to protect the patient breathing tube, face and neck, the surgeon to catch the patient during the turning of the patient, nurses to help lift the patient for the turning and protecting the legs as well as the multiple attachments on the patient such as IV accesses, EKG, blood pressure cuff/tubing, Foley catheter, etc. When everyone on the team is in position for the turning of the patient, communication is critical at this time. The anesthesiologist will call for attention and count to three. This is when everyone on the team together will turn the patient simultaneously.

After the turning of the patient, the secondary sheet 901 now can be detached by releasing the buckles 900 and Velcro attachments 903 from the device 10. It is important at this time to assure to avoid pressure on the critical organs of the patient's such as the eyes, nose, abdomen (for breathing), and the genital areas. The breathing tube must also be checked and again secured. All the pressured areas must be properly padded. At this point, the padded substrates 16 can be engaged to form wrapped engagements around the patient's arms and optionally the overlay substrate 18 can be engaged. At the end of the surgery, if the patient needs to be repositioned from prone to supine position, the process now can be reversed whereby the secondary sheet is reattached, the patient rolled back to a supine position whereby the device 10 can then be removed from the front of the patient.

Figure 34:
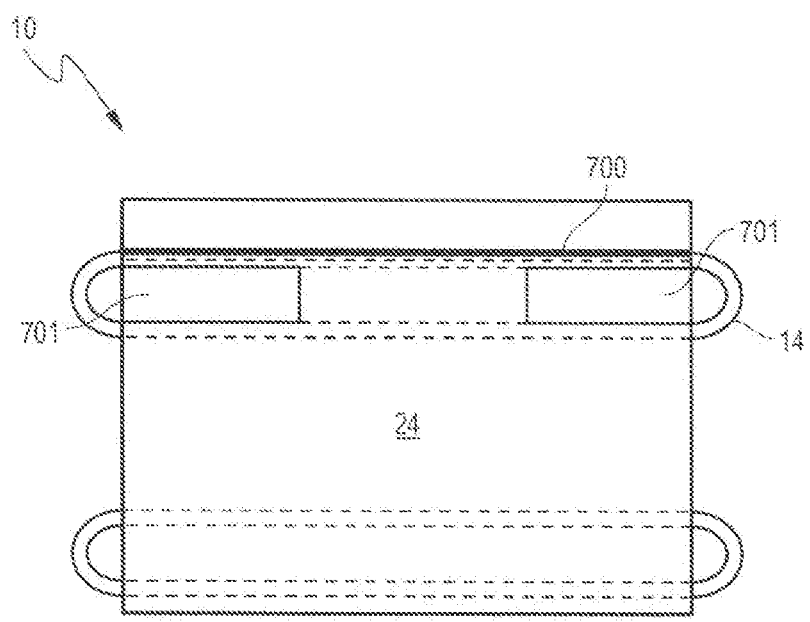
FIG. 34 depicts another embodiment of the patient positioning device of the present invention configured with pockets adapted to receive an axillary support.
Figure 35:
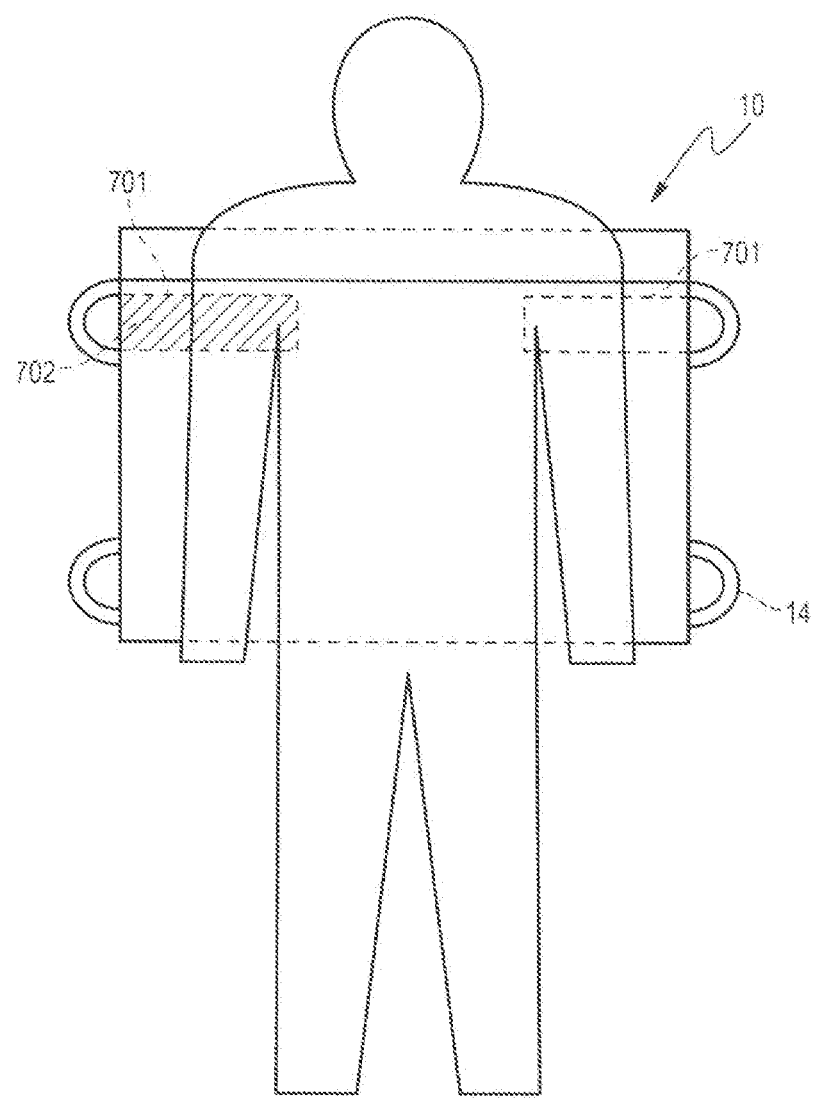
FIG. 35 depicts a top view of one embodiment of the patient positioning device of the present invention configured with pockets adapted to receive an axillary support with a patient thereon.
Figure 36:
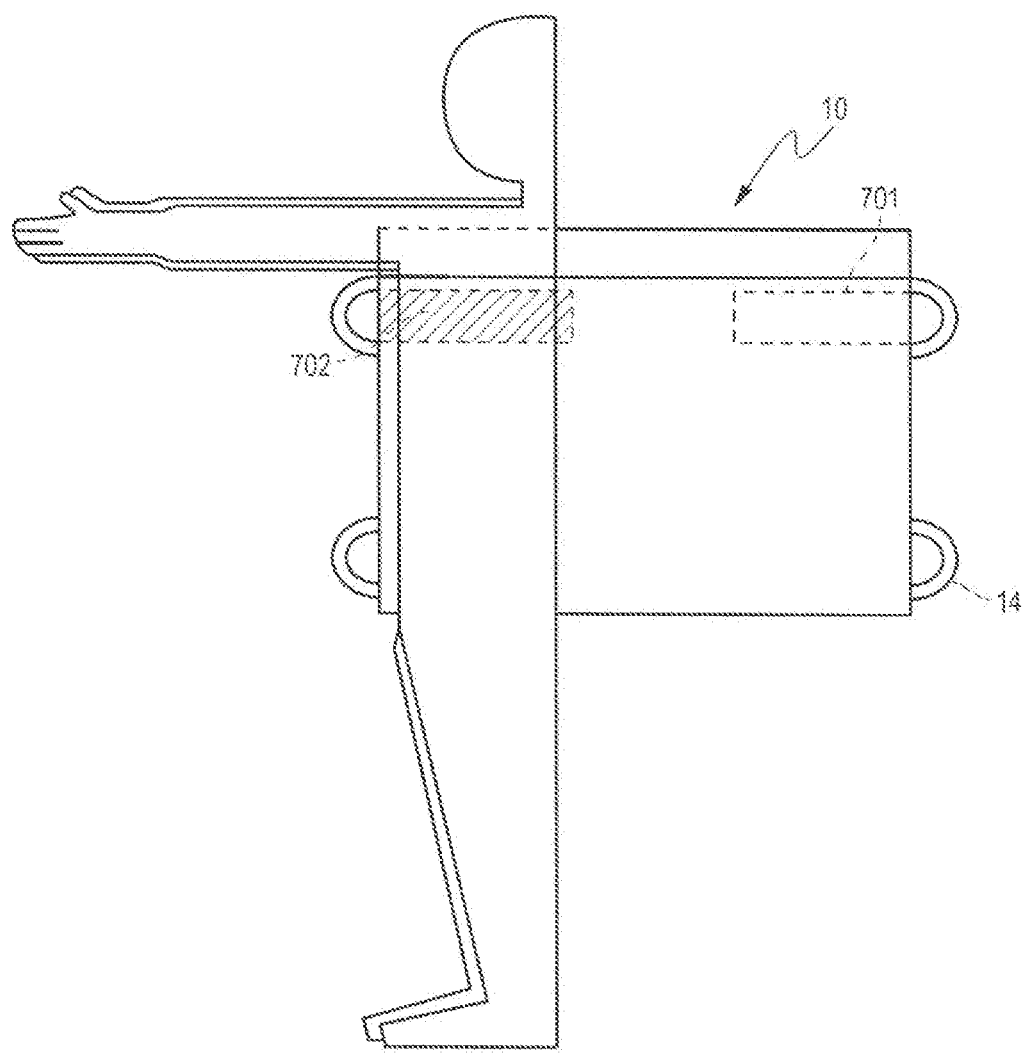
FIG. 36 depicts a top view of one embodiment of the patient positioning device of the present invention configured with pockets adapted to receive an axillary support with a patient in a lateral position.

In yet another embodiment of the device 10 of the present invention, structure may be provided to comfortably position a patient in a lateral orientation. As shown in FIG. 34, device 10 includes handles 14 and one or more rectangular pockets 701. Pockets 701, in some embodiments, are disposed toward the top of device 10 and are configured to align with the axillary line 700 of the device. This allows the pockets to be located proximal to the patient's armpits, or axillary region as shown in FIG. 35. The pockets 701 are adapted to receive a gel roll or a one liter fluid bag to be used as an axillary support 702 for the patient. In use, a patient is positioned on the top surface 24 of the device 10 aligning the pocket 701 with the "axillary roll" about one inch from the axilla of either side of the patient. After the patient is anesthetized, personnel are recruited to position the patient from the supine position to the lateral decubitus position with the axillary roll placed in the pocket 701 at the side that the patient will be positioned on, as shown in FIG. 36. For example, for right lateral decubitus, the axillary roll would be placed on the right pocket 701 prior to repositioning. The patient is then pulled to one side that is away from the "down" side and then rotated so that the operative side will be up and the decubitus side will be down. At this time the patient should be on the axillary roll to avoid pressure on the neurovascular bundle in the axilla (axillary nerve, artery and vein). At this time, fine adjustments should be performed to assure the patient is in the middle of the bed and secured to the operating room bed. The device 10 may further include the padded substrates 16 and overlap substrate 18 as provided throughout this disclosure.

Figure 37:
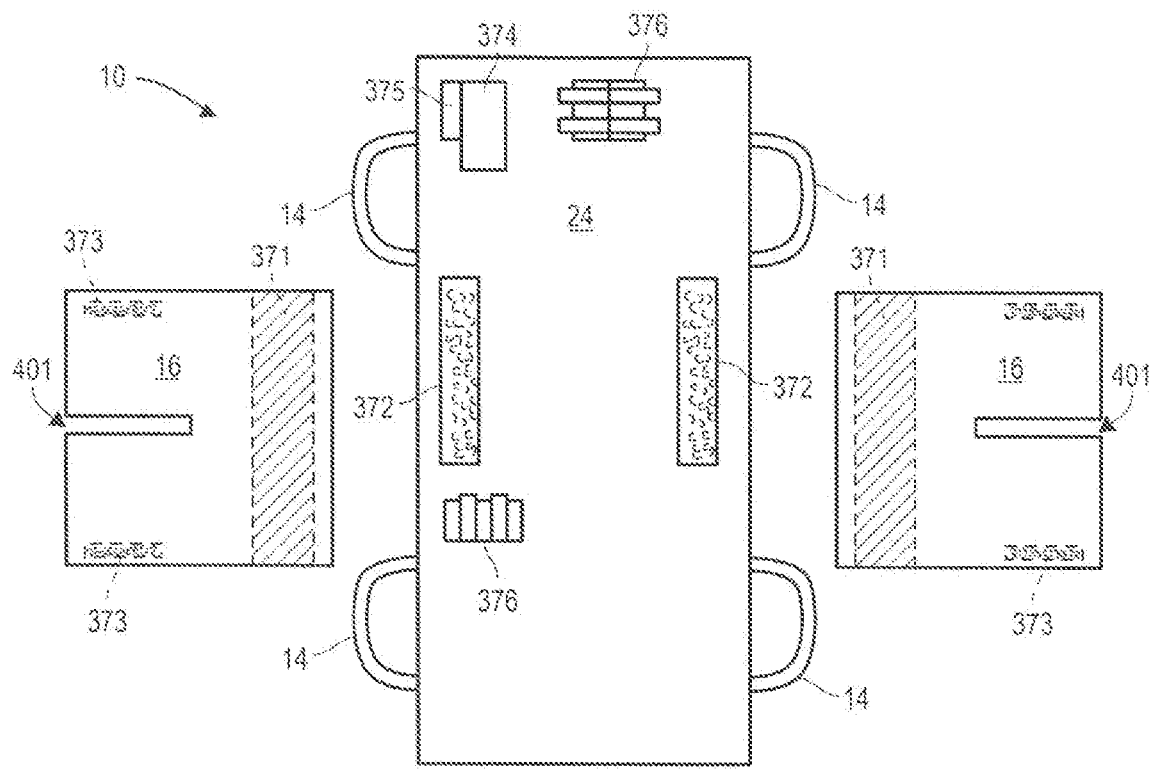
FIG. 37 depicts yet another embodiment of the present invention having various accessory features.
Figure 38:
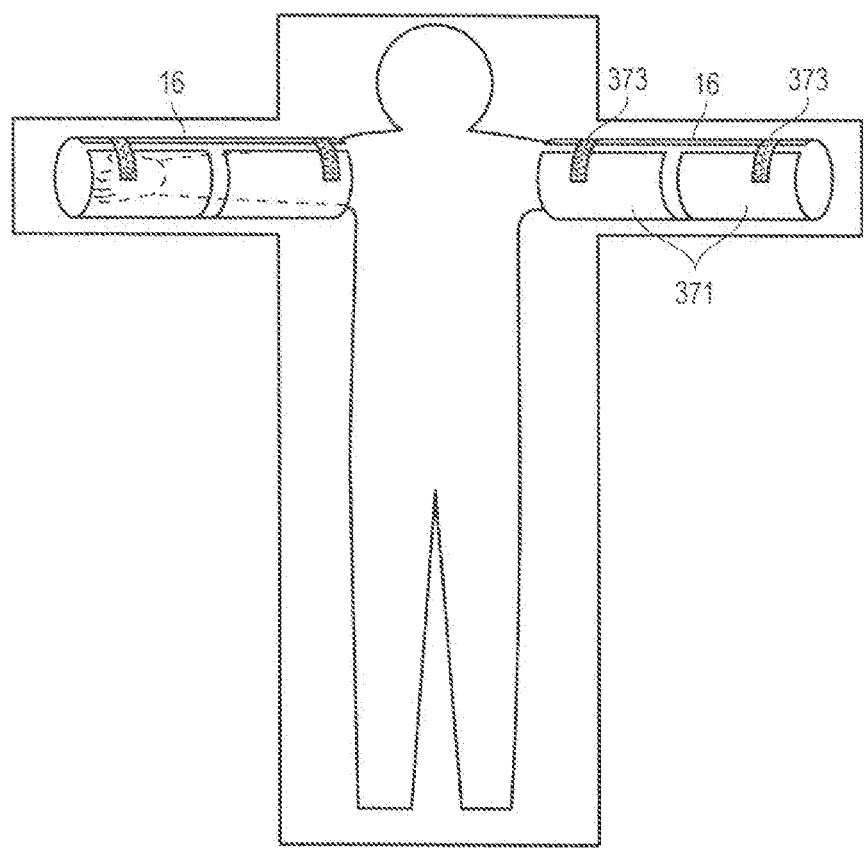
FIG. 38 depicts a patient with arms outstretched wrapped with the padded substrates of the device described herein.

In yet another embodiment of the device 10 of the present invention, several additional features and functionality are provided. With reference to FIGS. 37-38, shown is patient positioning device 10 having removable padded substrates 16 each have slits 401 as described above. The padded substrates 16 are attachable to the device 10 by way of hook and loop fasteners 371 provided on substrates 16 which engage corresponding hook and loop fasteners 372 on device 10. In some embodiments, the entire top surface of padded substrates 16 may comprise hook and loop fasteners 371. Thus, this embodiment removes the need for straps 40 in that the reverse side of the padded substrates 16 can include corresponding hook and loop strips 373 which allow the padded substrate 16 to be rolled over and doubled back on itself, securing and defining a wrapped engagement around a patient's arm or leg as shown in FIG. 38. Because the padded substrates 16 are removable from the device 10, they can be used as shown in FIG. 38 where the patient's arms are outstretched.

In some embodiments, a suction tip pocket 374 is provided to store the suction tip for the anesthesiologist. Next to this suction tip pocket is a side pocket 375 for kinking the suction tube to eliminate the annoying noise of the suctioning sound when the suction is not in use. hook/loop double-straps 376 may also be provided toward the top, middle, or bottom of device 10 to secure I.V. injection ports/arterial line/Swan Ganz catheter/EKG cable/or blood pressure tubing. The double strap design is necessary to keep the I.V. injection port between the straps to prevent sliding of the line. This same principle can be applied for Swan Ganz catheter or other lines. The double strap fasteners at the foot-end for the Foley catheter and chest tubes have additional loose Velcro strips with adhesive backing. These adhesive backing pieces are to be placed on the tube of the Foley catheter or chest tube. This is then placed in the hook/loop double-straps 376 to prevent the tube from sliding. Multiple loose hook/loop or Velcro strips can also be placed on the hook and loop surface 371 of the padded substrates 16 which serve to wrap the arms with the padded substrates 16 when they need to be placed on the arm boards shown in FIG. 38. They can also be used to organize the I.V. lines, cable, or tubes alongside the patient's arms.

Figure 39:
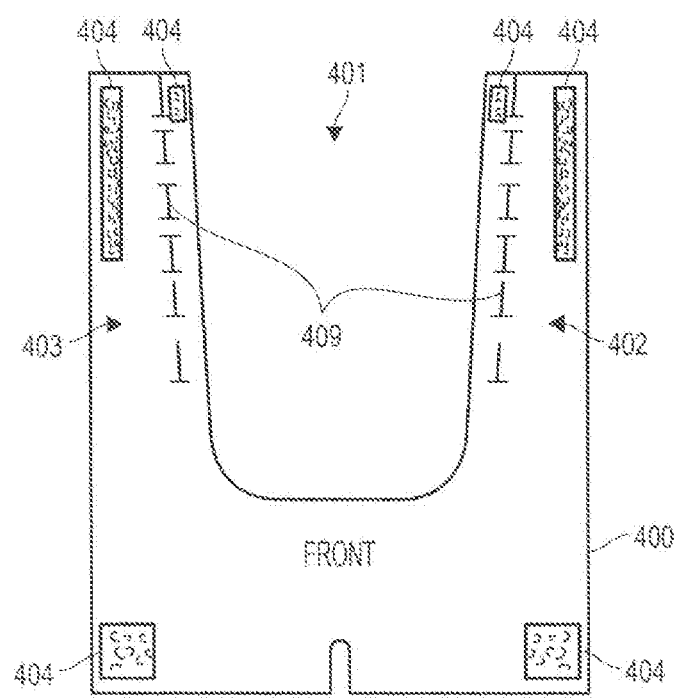
FIG. 39 depicts a top view of the front of a shoulder strap accessory for the patient positioning device of the present invention.
Figure 40:
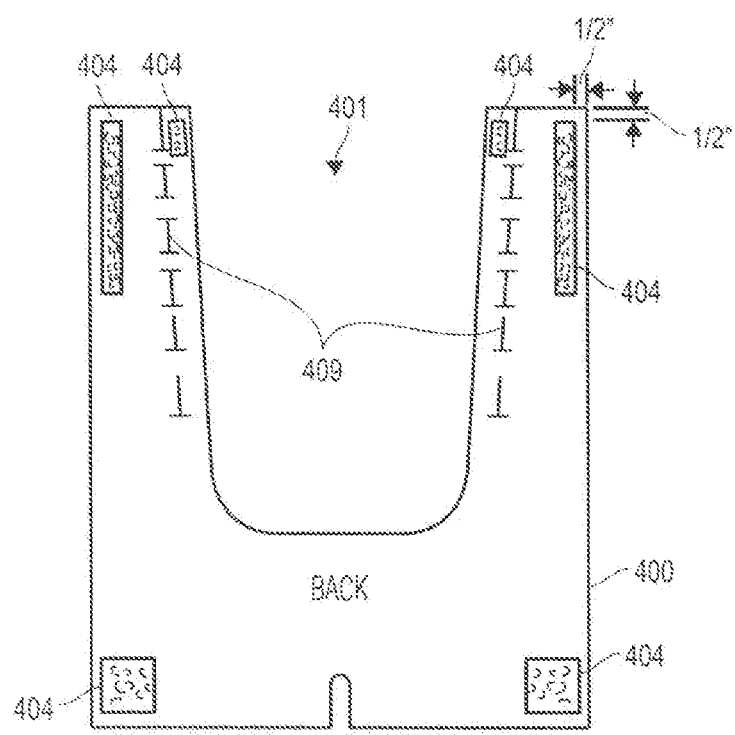
FIG. 40 depicts a top view of the back of a shoulder strap accessory for the patient positioning device of the present invention.
Figure 41:
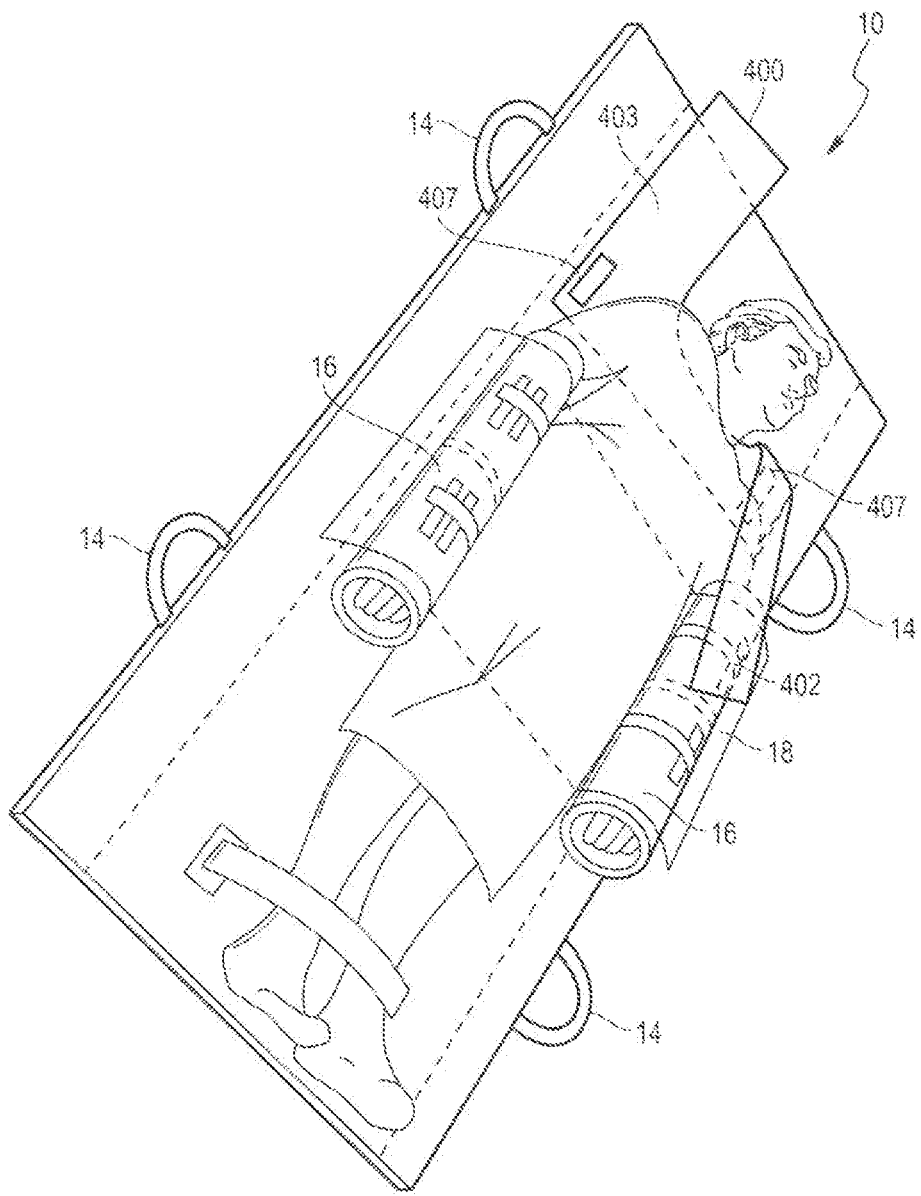
FIG. 41 depicts one embodiment of the shoulder strap in use in conjunction with the patient positioning device of the present invention.

To provide additional security and protection for the patient, a shoulder strapping system is also provided as an enhancement to patient positioning device 10. With reference to FIGS. 39-41 shown is a shoulder strap 400 comprising a substantially planar sheet having a U-shaped cutout 401 thus defining two strapping members 402 and 403. Each side of shoulder strap 400 includes one or more hook/loop fasteners 404. With reference to FIG. 41, the bottom portion 405 of the shoulder strap is configured to attach to corresponding hook/loop fasteners proximal to the shoulder area of the patient positioning device 10. The patient is then placed onto the device 10 and the strapping members 402 and 403 are carried over top of the patient's shoulders whereby they each can be secured to the padded substrates 16 by one or more hook/loop fasteners 404. In some embodiments, the padded substrates 16 may have corresponding hook/loop fasteners 407. Further, in some embodiments, the shoulder strap 400 includes perforation lines 409 which allow a portion of the strapping members 402 and 403 to remain attached to device 10 while the remaining portion is carried over the patient's shoulder and attached to the padded substrates 16. Accordingly, the distal ends of the strapping members 402 and 403 may include smaller hook/loop fasteners on the inside of the perforation lines 409. The shoulder strap 400 provides additional structure to secure the patient's upper body and arms and further serves to protect and elevate the patient's arms from the underlying support surface, i.e. the operating room table or gurney.

Figure 42:
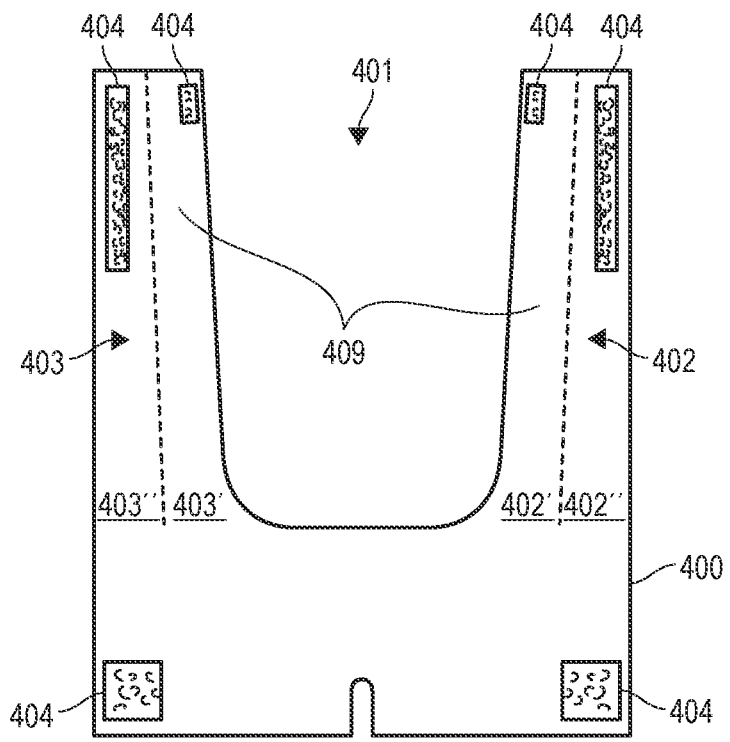
FIG. 42 depicts a top view of another embodiment of the shoulder strap.
Figure 43:
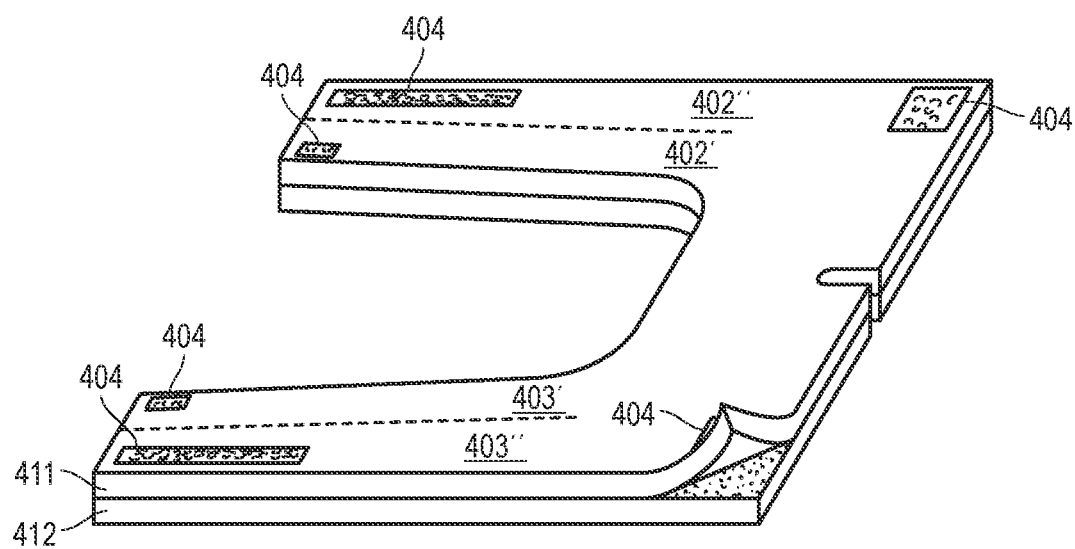
FIG. 43 depicts a side perspective view of the shoulder strap shown in FIG. 42.

In another embodiment, as shown in FIGS. 42-44, shoulder strap 400 comprises two layers of padded material. In some embodiments the upper layer 411 comprises a memory foam or similar padded material configured to conform to the patient's anatomy and to stabilize the patient and reduce the risk of pressure injury to the sacral and scapular areas during long procedures, particularly surgery. The bottom layer 412 comprises a foam material in combination with a laminated looped fabric, such as the "loop" Velcro material. The laminated foam material strengthens the bottom layer and provides a surface for attachment of various substrates, wrapments and accessories of device 10 as described in detail throughout this disclose. In some embodiments, the shoulder strap 410 comprises a substantially planar sheet having a U-shaped cutout 401 thus defining two strapping members 402 and 403 for each respective side of the patient's body. The strapping members 402 and 403 are divided lengthwise into two sections each inner section 402' and 403' and outer sections 402" and 403". In some embodiments, each of the strapping members 402 and sections thereof include one or more hook/loop fasteners 404.

Figure 44A:
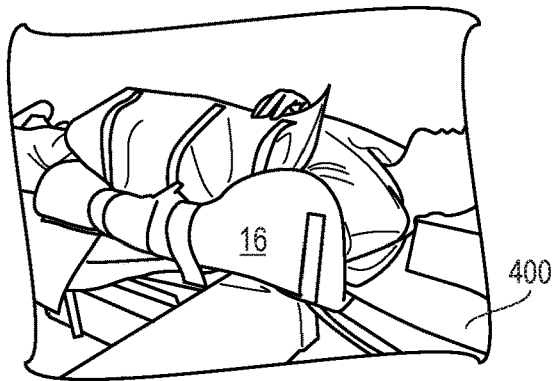
FIG. 44A shows the shoulder strap in use in a first step.
Figure 44B:
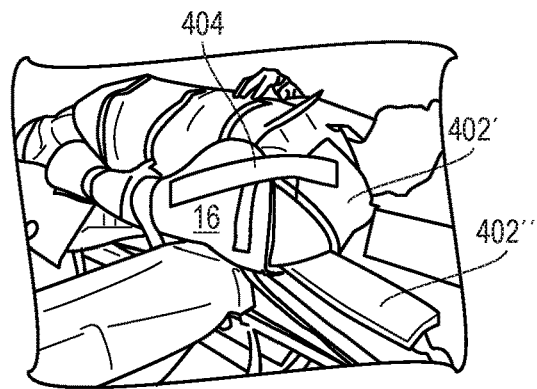
FIG. 44B shows the shoulder strap in use in a second step.
Figure 44C:
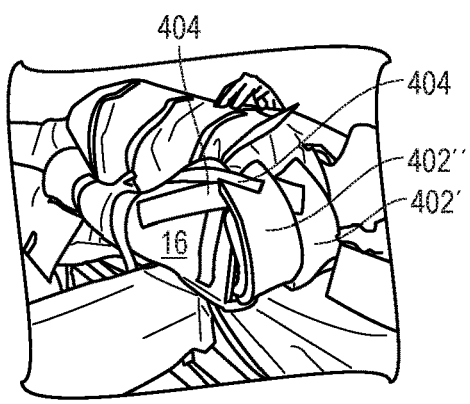
FIG. 44C shows the shoulder strap in use in a third step.
Figure 44D:
FIG. 44D shows the shoulder strap in use in a fourth step.
Figure 44E:
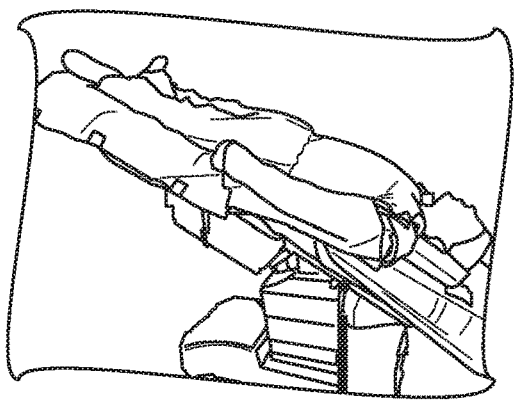
FIG. 44E shows the shoulder strap in use to secure and retain a patient in the Trendelenburg position.

In use, as shown in FIGS. 44A-44E, the inner section 402' and 403' of the respective strapping members wrap over the patient substantially at the trapezius muscle (FIG. 44B) and attach by hook/loop fastener to the patient positioning device 10, for example at the substrate 16 wrapped around the patient's arm most adjacent to the respective member of the shoulder strap 400. The outer section 402" and 403" of the respective strapping members wrap over the patient substantially at the shoulder cuff (FIG. 44C) and attach to the patient positioning device 10 at, for example, substrate 16. In some embodiments, additional hook/loop fastener material can be used to attach to respective inner and outer sections of the shoulder strap to one another. The overlap substrate 18 can then be placed over the arm/shoulder area to cover the attachment points (FIG. 44D). It is appreciated that the shoulder strap 410 can function as a stand-alone device or it can be adhered to or otherwise used in conjunction with patient positioning device 10.

The sectioned shoulder strap 400 provides a conforming "tailored" fit to the patient's anatomy, particularly at and around the shoulder and upper chest region. The shoulder strap 400 is particularly useful when the patient is placed in Trendellenburg position (tilting head-down—shown in FIG. 44E), whereby the strap 400 functions to distribute the patient's weight across the entire shoulder region which can significantly reduce the risk of brachial plexuses injury, a common injury that occurs during prolonged use of the Trendellenburg position. These advantageous occur due to the double-strapping of the shoulders at the shoulder cuff and the trapezius areas. Another advantage of the shoulder wrap 400 is to provide passive warming (covering and insulating) to the patient's shoulders and arms to help maintain patient's temperature, particularly when used in conjunction with the substrates of the device 10 and any forced warm-air features thereof.

Figure 45A:
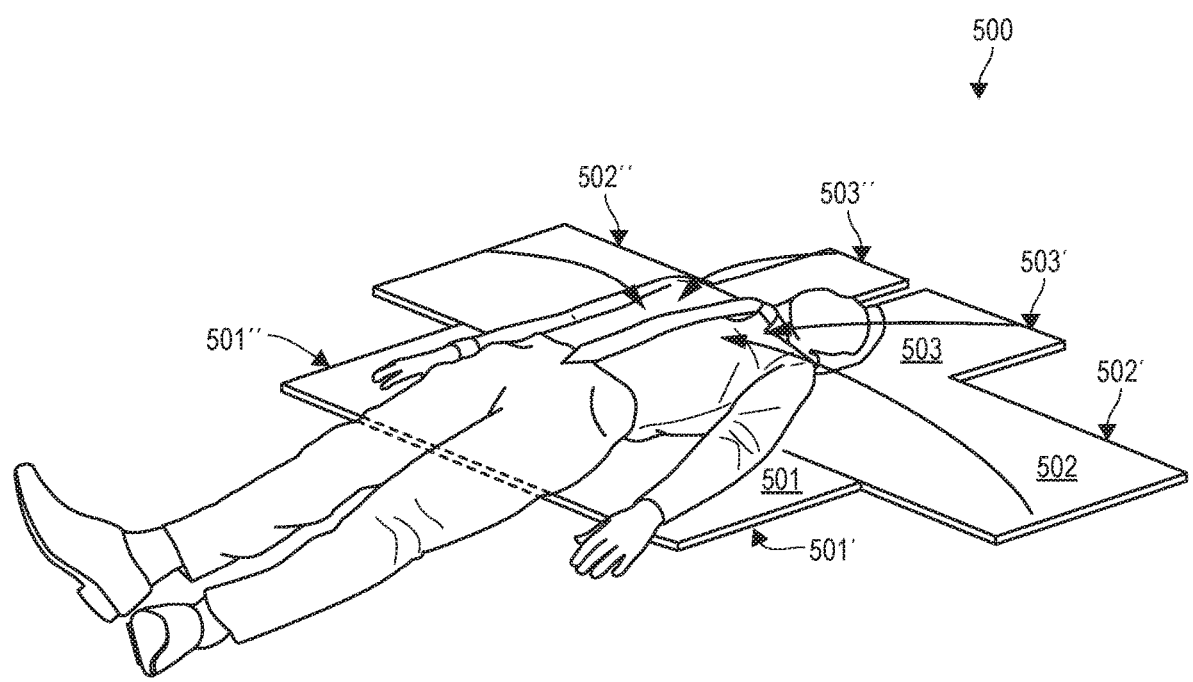
FIG. 45A depicts a body pad aspect of the present invention
Figure 45B:
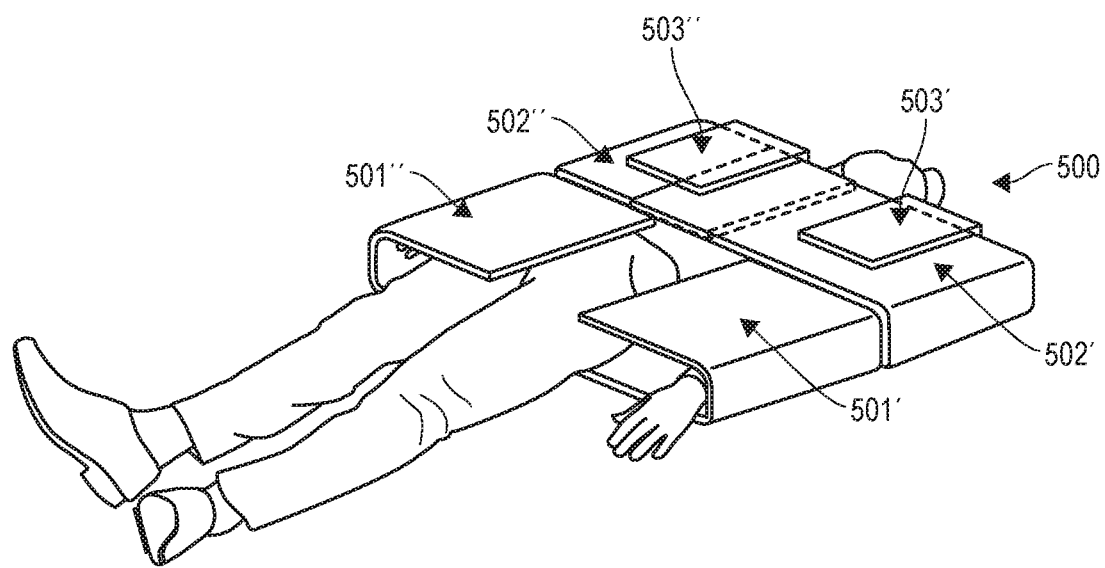
FIG. 45B depicts the body pad of FIG. 45A in use on an exemplary patient.

FIGS. 45A-45B depict yet another embodiment of the present invention configured as a multi-purpose pad 500 having a generally stepped T-shaped configuration. In some embodiments, the pad 500 comprises a durable foam material to provide protection, support, and warmth for the target patient. The pad 500 is divided into three sections, a lower section 501, a middle section 502, and an upper section 503. A patient is disposed on the pad 500 such that the lower section 501 is located substantially about the lower torso and lower arm and hand area of the patient. The middle section 502 is disposed substantially about the chest, upper torso, and upper arm area and is wider than the lower section 501. The upper section 503 is disposed substantially about the head and shoulder area of the patient and is the narrowest of the three sections 501, 502, and 503. Each of the sections 501, 502, and 503 are arranged to cover both sides of the body at the location at which they are disposed. In some embodiments, the lower section 501 includes a left and right arm wrap 501' and 501"(analogous to the padded substrates 16 in other embodiments), the middle section 502 includes left and right chest wraps 502' and 502", and the upper section 503 includes left and right shoulder wraps 503' and 503".

FIG. 45B shows the multipurpose pad 500 in use. To secure the patient who is provided on the pad 500, the left and right chest wraps 502' and 502" are overlapped over the patients' chest area and secured, for example, by hook and loop fastener or the like. Next, the left and right shoulder wraps 503' and 503" are each wrapped over the patient's shoulder and directed downward so as to attach to the respective left and right chest wraps 502' and 502". Attachment may be made by hook and loop fastener or the like attached at or near the end of each of the respective chest wraps 502' and 502". Next, in some embodiments the left and right arm wraps 501' and 501" are wrapped around a respective arm of the patient to protect, lift, and elevate the arms. In some embodiments, the pad 500 can be incorporated into or otherwise used in conjunction with the patient positioning device 10, for example, as a more robust replacement for the padded substrates 16 to secure the patient across the entire upper body at the arms, chest, torso, and shoulders to protect and secure the patient in various positions including but not limited to the Trendellenburg position. In other embodiments, the pad 500 can function as a standalone device to be attached to a gurney or operating table by way of one or hook and loop fastener straps, or similar strapping devices.

While specific embodiments have been described in detail, those with ordinary skill in the art will appreciate that various modifications and alternatives to those details could be developed in light of the overall teachings of the disclosures. Accordingly, the particular arrangements disclosed are meant to be illustrative only and not limiting of the invention, which is to be given the full breadth of the appended claims, and any and all equivalents thereof.

What is claimed is:

1. A shoulder strap for retaining and securing a patient, comprising:
    a U-shaped sheet defining two strapping members;
    wherein each of the strapping members are divided lengthwise into an inner section and an outer section;
    wherein the U-shaped sheet is configured to be disposed on the posterior of the shoulders of a patient whereby the strapping members are disposed over and around the shoulders and are configured to be removably secured to a substrate, such that (a) the inner section of each of the strapping members is configured to wrap over the patient substantially at a trapezius muscle and attach by hook/loop fastener to the substrate and (b) that the outer section of each of the strapping members is configured to wrap over the patient substantially at a shoulder cuff and attach by hook/loop fastener to the substrate; and
    wherein the inner and outer sections of each of the strapping members are divided by a perforation line.

2. The shoulder strap of claim 1, wherein the shoulder strap comprises an upper layer of foam and a bottom layer of a combined foam and looped fastener material.

* * * * *